(12) United States Patent
Mahadik et al.

(10) Patent No.: US 12,336,774 B2
(45) Date of Patent: Jun. 24, 2025

(54) OPERATING DEVICES IN AN OPERATING ROOM

(71) Applicant: Stryker Corporation, Kalamazoo, MI (US)

(72) Inventors: Amit A. Mahadik, San Jose, CA (US); Ramanan Paramasivan, San Jose, CA (US); Suraj Bhat, Fremont, CA (US); Afshin Jila, San Jose, CA (US); Manoj Aggarwal, Gurgaon (IN); Sourabh Choudhary, Palwal (IN)

(73) Assignee: Stryker Corporation, Portage, MI (US)

( * ) Notice: Subject to any disclaimer, the term of this patent is extended or adjusted under 35 U.S.C. 154(b) by 1083 days.

(21) Appl. No.: 17/138,777

(22) Filed: Dec. 30, 2020

(65) Prior Publication Data

US 2021/0196406 A1 Jul. 1, 2021

Related U.S. Application Data

(60) Provisional application No. 62/956,012, filed on Dec. 31, 2019.

(51) Int. Cl.
*G16H 40/63* (2018.01)
*A61B 34/00* (2016.01)
*A61B 90/00* (2016.01)
*G16H 30/20* (2018.01)

(52) U.S. Cl.
CPC ............ *A61B 34/25* (2016.02); *A61B 90/361* (2016.02); *G16H 30/20* (2018.01); *G16H 40/63* (2018.01); *A61B 2560/0487* (2013.01)

(58) Field of Classification Search
None
See application file for complete search history.

(56) References Cited

U.S. PATENT DOCUMENTS

| 7,287,278 | B2 | 10/2007 | Liang |
| 8,347,389 | B2 | 1/2013 | Kulkarni et al. |
| 8,424,062 | B2 * | 4/2013 | Sanchez ............... H04L 63/105 455/406 |

(Continued)

OTHER PUBLICATIONS

International Preliminary Report on Patentability dated Jul. 5, 2022, directed to International Application No. PCT/US2020/067551; 7 pages.

(Continued)

*Primary Examiner* — Robert A Sorey
(74) *Attorney, Agent, or Firm* — Morrison & Foerster LLP

(57) ABSTRACT

Described are methods and systems for operating devices in an operating room (OR), according to some embodiments. An OR hub can provide an operations user interface (UI) that is provisioned by a hub software developer to enable authorized users to access permitted software functions run by the system software on the OR hub to operate one or more medical devices in the OR. The operations UI can be configured to prevent an interaction of the one or more medical devices and the OR hub with a user until that user is authenticated through the operations U. In some embodiments, the operations UI of the OR hub implements role-based security in which the operations UI provides an authenticated user with different sets of permitted software and/or security functions based on a type of credential possessed by the authenticated user.

30 Claims, 13 Drawing Sheets

(56) References Cited

U.S. PATENT DOCUMENTS

| | | | | |
|---|---|---|---|---|
| 9,349,021 | B1* | 5/2016 | Chaganti | G06F 21/6218 |
| 10,007,408 | B2 | 6/2018 | Marka et al. | |
| 2006/0026687 | A1 | 2/2006 | Peikari | |
| 2006/0218394 | A1* | 9/2006 | Yang | G06F 21/604 |
| | | | | 713/165 |
| 2012/0066508 | A1* | 3/2012 | Lentini | G06F 21/6245 |
| | | | | 713/186 |
| 2013/0190674 | A1* | 7/2013 | Case | G16H 40/67 |
| | | | | 604/6.01 |
| 2018/0289387 | A1* | 10/2018 | Khajavi | G16H 40/63 |
| 2019/0006031 | A1* | 1/2019 | Hyde | G16H 40/20 |
| 2020/0218817 | A1* | 7/2020 | Thrower | G06F 21/35 |
| 2022/0199208 | A1* | 6/2022 | McFarlane | G06Q 40/08 |
| 2022/0222734 | A1* | 7/2022 | Rosinko | G06Q 10/087 |

OTHER PUBLICATIONS

International Search Report and Written Opinion Mailed Mar. 22, 2021, directed to International Application No. PCT/US2020/067551; 12 pages.

Maquet—Getinge Group. (2012). "Tegris Redefining OR Integration," Brochure; 16 pages.

Stryker Corporation. (2014). "SwitchPoint Infinity 2—Control System Operations and Maintenance Manual"; 82 pages.

Examination Report dated Dec. 23, 2024, directed to EP Application No. 20845853.9; 5 pages.

* cited by examiner

900B

Access Control  Shipment Repair

Date & Time

902 — Network Time Protocol (NTP) [On]

Time Zone: (UTC-08:00) Pacific Time (US & Canada)
Date Format: mm/dd/yyyy

Month: − 7 +
Day: − 9 +
Year: − 2019 +

Hour: − 9 +
Minute: − 23 +
AM/PM: AM

904 — Server Address | Port Number

FIG. 9B

OPERATING DEVICES IN AN OPERATING ROOM

CROSS-REFERENCE TO RELATED APPLICATIONS

This application claims the benefit of U.S. Provisional Application No. 62/956,012, filed Dec. 31, 2019, the entire contents of which are hereby incorporated by reference herein.

FIELD OF THE DISCLOSURE

This disclosure relates generally to systems and methods for operating devices in an operating room, in particular for securing operation of medical devices.

BACKGROUND OF THE DISCLOSURE

Current operating rooms include many disjointed medical and networked devices that assist hospital personnel in performing surgical procedures. Such devices include, for example, surgical lights, endoscope cameras, insufflators, touch panels, and hospital servers. As more medical devices are being connected to a network, securing their operation is becoming a critical concern. This is in part because connecting the medical devices to the network weakens the security posture of the operating room environment. Moreover, many medical devices are shared or rotated between different operating rooms or across different locations of a hospital. The shared nature of these medical devices increases the risk for patient data and software compromise because moving the medical devices between locations exposes them to unauthorized individuals. Any surgical or networked device that is or becomes compromised in the operating room environment may significantly impact an ongoing surgical procedure-including prolonging a duration of the surgical procedure or result in adverse outcomes for a patient.

SUMMARY OF THE DISCLOSURE

To address the challenges discussed above, there exists a need for systems and methods for operating devices in an operating room (OR). In some embodiments, an OR hub can provide an operations user interface (UI) to enable authorized users to access permitted software functions run by the system software on the OR hub to operate one or more medical devices in the OR. The operations UI can be configured to prevent an interaction of the one or more medical devices and the OR hub with a user until that user is authenticated through the operations U. In some embodiments, the operations UI of the OR hub implements role-based security in which the operations UI provides an authenticated user with different sets of permitted software and/or security functions based on a type of credential possessed by the authenticated user. Therefore, the operations UI serves as a restricted interface through which authorized users can access preauthorized functionality of the OR hub.

In some embodiments, a method for operating devices in an operating room comprises: at an operating room (OR) hub coupled to one or more medical devices in the operating room: preventing a user from interacting with the one or more medical devices until the user is authenticated though an operations user interface (UI) during a surgical procedure of a patient; permitting, via the operations UI, a medical practitioner having an operator credential to operate the one or more medical devices during the surgical procedure according to a plurality of permitted software functions, but preventing the medical practitioner from changing one or more device access privileges of the OR hub and changing the plurality of permitted software functions; permitting, via the operations UI, a hospital network administrator having an administrator credential to change the operator credential of the medical practitioner, but preventing the hospital network administrator from changing the plurality of permitted software functions; and permitting a hub software developer having a developer credential to configure the plurality of permitted software functions, wherein the operations UI is configured to prevent any hospital personnel having the operator credential or the administrator credential from altering metadata generated at the OR hub based on user interactions with the operations UI.

In some embodiments, the method comprises running system software to operate a firewall on the OR hub to control inbound and outbound network connections to the operating room.

In some embodiments, the system software comprises an operating system of the OR hub.

In some embodiments, the system software is configured to allow the plurality of permitted software functions corresponding to the one or more medical devices to run on the OR hub.

In some embodiments, the method comprises: permitting, via the operations UI, the hospital network administrator having the administrator credential to select one of a plurality of permitted communication protocols to configure a network connection between the OR hub and a networked device outside the operating room; and automatically provisioning a firewall to allow the configured network connection. In some embodiments, the method comprises: permitting, via the operations UI, the medical practitioner having the operator credential to access the networked device via the network connection preconfigured by the hospital network administrator.

In some embodiments, the method comprises: enabling the network connection when the medical practitioner is permitted to operate the one or more medical devices during the surgical procedure; and disabling the network connection to the networked device when the medical practitioner is logged out of the operations UI.

In some embodiments, to configure the network connection between the OR hub and the networked device, the method comprises: prompting, via the operations UI, the hospital network administrator to select a network port of the OR hub and a device identifier of the networked device.

In some embodiments, the networked device comprises an SFTP server or a DICOM server.

In some embodiments, the one or more medical devices comprises surgical lights, an endoscope camera, an insufflator, an audio and video (AV) router, or a printer.

In some embodiments, the method comprises: permitting, via the operations UI, the medical practitioner having the operator credential to access patient data generated by the OR hub or the one or more surgical devices during the surgical procedure. In some embodiments, the method comprises: storing patient data on an encrypted memory of the OR hub, the patient data generated based on user interactions between the medical practitioner and the operations UI during the surgical procedure. In some embodiments, the patient data comprises audio, video, or textual data generated by one or more permitted software functions of the permitted software functions accessed by the medical practitioner during the surgical procedure.

In some embodiments, the one or more medical devices comprise an endoscope camera, and wherein the patient data comprises an image or a video captured by the endoscope camera.

In some embodiments, the method comprises: permitting, via the operations UI, the hospital network administrator having the administrator credential to select one of a plurality of permitted communication protocols to configure a network connection between the OR hub and a networked device outside of the operating room; and automatically provisioning the firewall to allow the configured network connection.

In some embodiments, the method comprises: permitting, via the operations UI, the medical practitioner to select the networked device for exporting the patient data outside of the operating room through the network connection previously configured by the hospital network administrator.

In some embodiments, the method comprises: permitting, via the operations UI, the hospital network administrator to individually enable or disable communication ports of the OR hub to control local connections between the OR hub and the one or more medical devices.

In some embodiments, the communication ports comprise a USB port or a serial port.

In some embodiments, the method comprises: restricting, via the operations UI, the medical practitioner having the operator credential from accessing the metadata generated at the OR hub; and permitting, via the operations UI, the hospital network administrator having the administrator credential to view the metadata.

In some embodiments, the method comprises: coupling the OR hub to a touch panel; and providing the operations user interface (UI) for display on the touch panel.

In some embodiments, permitting the medical practitioner to operate the one or more medical devices comprises: configuring settings of surgical lights, an endoscope camera, or an insufflator based on inputs of the medical practitioner received by the operations UI.

In some embodiments, the method comprises: permitting, by the operations UI, the hospital network administrator having the administrator credential to assign the operator credential to one or more other medical practitioners to allow the one or more other medical practitioners to operate the one or more medical devices and to access one or more preconfigured network connections during surgical procedures.

In some embodiments, the method comprises: preventing, via the operations UI, any hospital personnel from executing software functions other than one or more of the plurality of permitted software functions set by the hub software developer.

In some embodiments, the method comprises: permitting, via the operations UI, the hospital network administrator having the administrator credential to run one or more security functions from a plurality of permitted security functions installed on the OR hub.

In some embodiments, the one or more security functions comprise an anti-virus scanner, and wherein the method comprises: precluding the anti-virus scanner from executing during the surgical procedure; and permitting, via the operations UI, the hospital network administrator to initiate the anti-virus scanner to scan the OR hub during a non-operative mode of the OR hub.

In some embodiments, the developer credential comprises information inputted to a removable media storage. In some embodiments, the method comprises: prompting the hub software developer to input the developer credential when the removable media storage is coupled to the OR hub; and permitting the hub software developer to configure the plurality of permitted software functions upon verifying the developer credential.

In some embodiments, an operating room (OR) hub for operating devices in an operating room, comprises: one or more processors; memory; and one or more programs, wherein the one or more programs are stored in the memory and configured to be executed by the one or more processors, the one or more program including instructions for: preventing a user from interacting with the one or more medical devices until the user is authenticated though an operations user interface (UI) during a surgical procedure of a patient; permitting, via the operations UI, a medical practitioner having an operator credential to operate the one or more medical devices during the surgical procedure according to a plurality of permitted software functions, but preventing the medical practitioner from changing one or more device access privileges of the OR hub and changing the plurality of permitted software functions; permitting, via the operations UI, a hospital network administrator having an administrator credential to change the operator credential of the medical practitioner, but preventing the hospital network administrator from changing the plurality of permitted software functions; and permitting a hub software developer having a developer credential to configure the plurality of permitted software functions, wherein the operations UI is configured to prevent any hospital personnel having the operator credential or the administrator credential from altering metadata generated at the OR hub based on user interaction with the operations UI.

In some embodiments, the instructions comprise: running system software to operate a firewall on the OR hub to control inbound and outbound network connections to the operating room.

In some embodiments, the system software comprises an operating system of the OR hub. In some embodiments, the system software is configured to allow the plurality of permitted software functions corresponding to the one or more medical devices to run on the OR hub.

In some embodiments, the instructions comprise: permitting, via the operations UI, the hospital network administrator having the administrator credential to select one of a plurality of permitted communication protocols to configure a network connection between the OR hub and a networked device outside the operating room; and automatically provisioning a firewall to allow the configured network connection.

In some embodiments, the instructions comprise: permitting, via the operations UI, the medical practitioner having the operator credential to access the networked device via the network connection preconfigured by the hospital network administrator.

In some embodiments, the instructions comprise: enabling the network connection when the medical practitioner is permitted to operate the one or more medical devices during the surgical procedure; and disabling the network connection to the networked device when the medical practitioner is logged out of the operations UI.

In some embodiments, to configure the network connection between the OR hub and the networked device, the instructions comprise: prompting, via the operations UI, the hospital network administrator to select a network port of the OR hub and a device identifier of the networked device.

In some embodiments, the networked device comprises an SFTP server or a DICOM server.

In some embodiments, the one or more medical devices comprises surgical lights, an endoscope camera, an insufflator, an audio and video (AV) router, or a printer.

In some embodiments, the instructions comprise: permitting, via the operations UI, the medical practitioner having the operator credential to access patient data generated by the OR hub or the one or more surgical devices during the surgical procedure. In some embodiments, the instructions comprise: storing patient data on an encrypted memory of the OR hub, the patient data generated based on user interactions between the medical practitioner and the operations UI during the surgical procedure. In some embodiments, the instructions comprise: the patient data comprises audio, video, or textual data generated by one or more permitted software functions of the permitted software functions accessed by the medical practitioner during the surgical procedure.

In some embodiments, the one or more medical devices comprise an endoscope camera, and wherein the patient data comprises an image or a video captured by the endoscope camera.

In some embodiments, the instructions comprise: permitting, via the operations UI, the hospital network administrator having the administrator credential to select one of a plurality of permitted communication protocols to configure a network connection between the OR hub and a networked device outside of the operating room; and automatically provisioning the firewall to allow the configured network connection.

In some embodiments, the instructions comprise: permitting, via the operations UI, the medical practitioner to select the networked device for exporting the patient data outside of the operating room through the network connection previously configured by the hospital network administrator.

In some embodiments, the instructions comprise: permitting, via the operations UI, the hospital network administrator to individually enable or disable communication ports of the OR hub to control local connections between the OR hub and the one or more medical devices.

In some embodiments, the communication ports comprise a USB port or a serial port.

In some embodiments, the instructions comprise: restricting, via the operations UI, the medical practitioner having the operator credential from accessing the metadata generated at the OR hub; and permitting, via the operations UI, the hospital network administrator having the administrator credential to view the metadata.

In some embodiments, the instructions comprise: coupling the OR hub to a touch panel; and providing the operations user interface (UI) for display on the touch panel.

In some embodiments, wherein permitting the medical practitioner to operate the one or more medical devices comprises: configuring settings of surgical lights, an endoscope camera, or an insufflator based on inputs of the medical practitioner received by the operations UI.

In some embodiments, the instructions comprise: permitting, by the operations UI, the hospital network administrator having the administrator credential to assign the operator credential to one or more other medical practitioners to allow the one or more other medical practitioners to operate the one or more medical devices and to access one or more preconfigured network connections during surgical procedures.

In some embodiments, the instructions comprise: preventing, via the operations UI, any hospital personnel from executing software functions other than one or more of the plurality of permitted software functions set by the hub software developer.

In some embodiments, the instructions comprise: permitting, via the operations UI, the hospital network administrator having the administrator credential to run one or more security functions from a plurality of permitted security functions installed on the OR hub.

In some embodiments, the one or more security functions comprise an anti-virus scanner, and the instructions comprise: precluding the anti-virus scanner from executing during the surgical procedure; and permitting, via the operations UI, the hospital network administrator to initiate the anti-virus scanner to scan the OR hub during a non-operative mode of the OR hub.

In some embodiments, the developer credential comprises information inputted to a removable media storage. In some embodiments, the instructions comprise: prompting the hub software developer to input the developer credential when the removable media storage is coupled to the OR hub; and permitting the hub software developer to configure the plurality of permitted software functions upon verifying the developer credential.

In some embodiments, a method for operating devices in an operating room comprises: at an operating room (OR) hub coupled to one or more medical devices in the operating room and providing an operations user interface (UI): displaying, via the operations UI, a login prompt to a user to prevent a user from interacting with the one or more surgical devices until the user is authenticated during a surgical procedure of a patient; in response to authenticating a medical practitioner as having an operator credential: displaying, via the operations UI, a plurality of graphical elements that correspond to a plurality of permitted software functions, wherein a selection of a graphical element permits the medical practitioner to operate the one or more medical devices according to a permitted software function corresponding to the selected graphical element, and wherein the medical practitioner is prevented from changing one or more device access privileges of the OR hub and changing the plurality of permitted software functions; in response to authenticating a hospital network administrator as having an administrator credential: displaying, via the operations UI, a panel that permits the hospital network administrator to change the operator credential of the medical practitioner, wherein the hospital network administrator is prevented from changing the plurality of permitted software functions; and in response to authenticating a hub software developer as having a developer credential: permitting the hub software developer to configure the plurality of permitted software functions, wherein the operations UI is configured to prevent any hospital personnel having the operator credential or the administrator credential from altering metadata generated at the OR hub based on user interaction with the operations UI.

In some embodiments, a non-transitory computer-readable storage medium comprises one or more programs for operating devices in an operating room using an operating room (OR) hub, wherein the one or more programs, when executed by one or more processors, cause the one or more processors to perform operations comprising: preventing a user from interacting with the one or more medical devices until the user is authenticated though an operations user interface (UI) during a surgical procedure of a patient; permitting, via the operations UI, a medical practitioner having an operator credential to operate the one or more medical devices during the surgical procedure according to a plurality of permitted software functions, but preventing the medical practitioner from changing one or more device access privileges of the OR hub and changing the plurality of permitted software functions; permitting, via the operations UI, a hospital network administrator having an administrator credential to change the operator credential of the medical practitioner, but preventing the hospital network administrator from changing the plurality of permitted software functions; and permitting a hub software developer having a developer credential to configure the plurality of permitted software functions, wherein the operations UI is configured to prevent any hospital personnel having the operator credential or the administrator credential from altering metadata generated at the OR hub based on user interaction with the operations UI.

BRIEF DESCRIPTION OF THE DRAWINGS

The foregoing summary, as well as the following detailed description of embodiments, is better understood when read in conjunction with the appended drawings. For the purpose of illustrating the present disclosure, the drawings show example embodiments of the disclosure; the disclosure, however, is not limited to the specific methods and instrumentalities disclosed. In the drawings:

FIGS. 9A-B are example screens that illustrates how an operations UI of an OR hub permits a user having an administrator credential to set a date and time of the OR hub, according to some embodiments;

DETAILED DESCRIPTION OF THE DISCLOSURE

Figure 1:
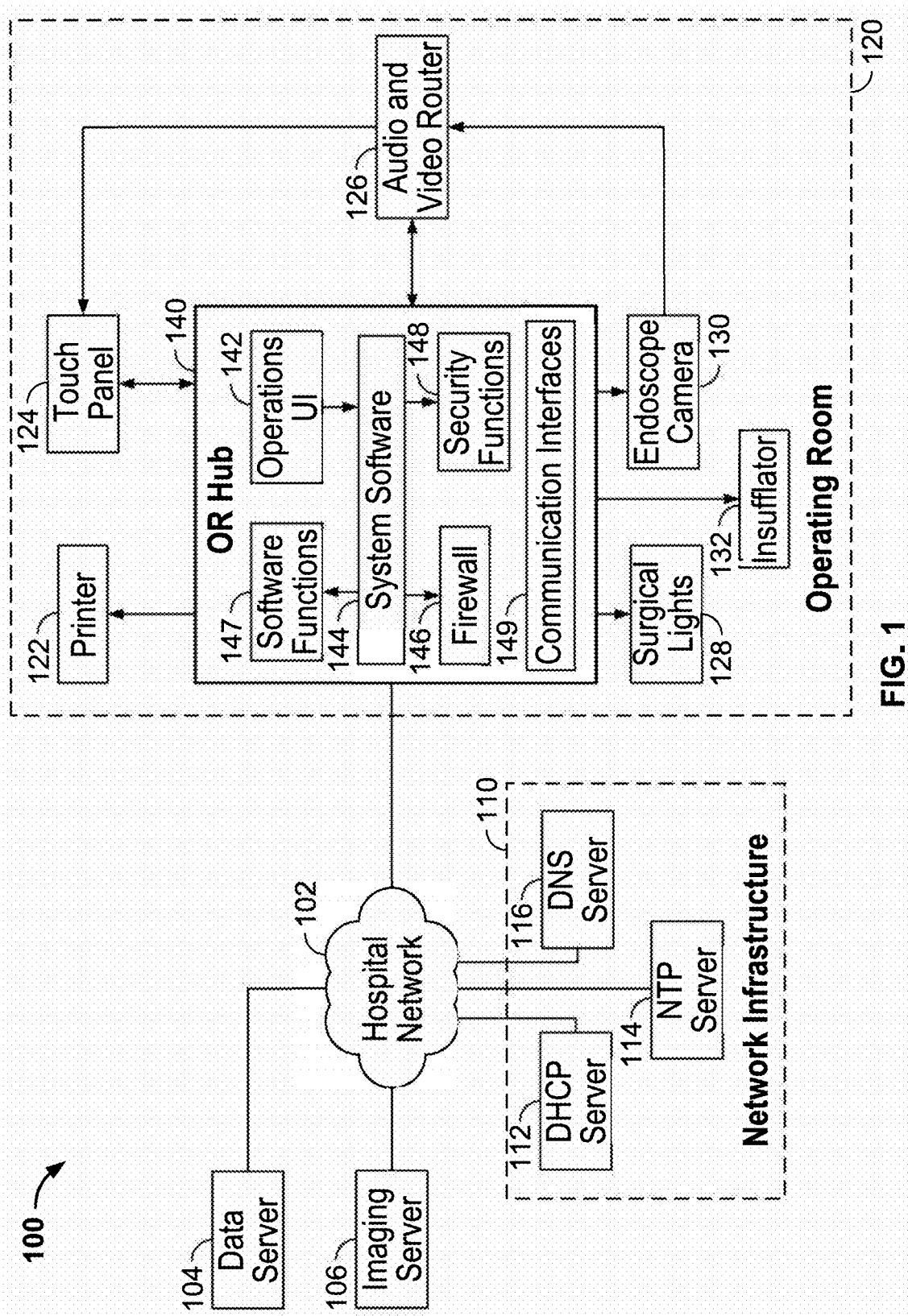
FIG. 1 is a diagram of a system including an operating room (OR) hub for operating devices in an operating room, according to some embodiments.

As described above, devices being used in operating rooms need to improve their cybersecurity posture to not only secure patient data, but also ensure that surgical procedures are not adversely impacted. In some embodiments, an Operating Room (OR) hub can be provided within an operating room to connect to and secure use of devices (e.g., medical devices) within the operating room. The OR hub includes system software (e.g., an operating system) that manages and controls hardware resources to communicate with and operate application software installed on the OR hub to enable one or more medical devices to be operated according to installed software. In some embodiments, the OR hub can include system software, application software, and firmware provisioned and preconfigured by a hub software developer to restrict how authorized users can interact with the OR hub.

In some embodiments, the OR hub can provide an operations user interface (UI) that is provisioned by the hub software developer to enable authorized users to access permitted software functions run by the system software to operate the one or more medical devices. To improve the cybersecurity posture of the operating room, the operations UI can be configured to prevent an interaction of the one or more medical devices and the OR hub with a user until that user is authenticated through the operations UI during a surgical procedure of a patient. In effect, the operations UI provides the user with a restricted interface to the system software, which reduces the possible threat vectors that can lead to the OR hub or any of its coupled devices becoming compromised. In some embodiments, the operations UI of the OR hub implements role-based security in which the operations UI provides an authenticated user with different sets of permitted software and/or security functions based on a type of credential possessed by the authenticated user.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic, or optical signals capable of being stored, transferred, combined, compared, and otherwise manipulated. It is convenient at times, principally for reasons of common usage, to refer to these signals as bits, values, elements, symbols, characters, terms, numbers, or the like. Furthermore, it is also convenient at times to refer to certain arrangements of steps requiring physical manipulations of physical quantities as modules or code devices without loss of generality.

All of these and similar terms, however, are to be associated with the appropriate physical quantities and are merely convenient labels applied to these quantities. Unless specifically stated otherwise as apparent from the following discussion, it is appreciated that, throughout the description, discussions utilizing terms such as "processing," "computing," "calculating," "determining," "displaying," or the like refer to the action and processes of a computer system, or similar electronic computing device, that manipulates and transforms data represented as physical (electronic) quantities within the computer system memories or registers or other such information storage, transmission, or display devices.

Certain aspects of the present invention include process steps and instructions described herein in the form of a method. It should be noted that the process steps and instructions of the present invention could be embodied in software, firmware, or hardware, and, when embodied in software, they could be downloaded to reside on, and be operated from, different platforms used by a variety of operating systems.

As used herein, the singular forms "a," "an," and "the" used in the following description are intended to include the plural forms as well unless the context clearly indicates otherwise.

It is to be understood that the term "and/or" as used herein refers to and encompasses any and all possible combinations of one or more of the associated listed items.

It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

FIG. 1 is a diagram of a system 100 including an operating room (OR) hub 140 for operating devices in an operating room 120, according to some embodiments. In some embodiments, OR hub 140 can control user access to and/or operation of one or more medical devices in operating room 120, data communication between devices within operating room 120, and inbound and outbound network connections to and from operating room 120.

In some embodiments, OR hub 140 can be communicatively coupled to a plurality of medical devices (e.g., surgical devices or electrical medical equipment) and one or more displays used during a surgical procedure. Such medical devices may include, for example, printer 122, touch panel 124, audio and video router 126, surgical lights 128, endoscope camera 130, and insufflator 132, each of which are commonly used during surgical procedures.

In some embodiments, audio and video router 126 can be communicatively coupled to one or more of endoscope camera 130, touch panel 124, and OR hub 140. For example, audio and video router 126 may be connected to touch panel 124 through an HDMI connection and connected to endoscope camera 130 through a High-definition Multimedia Interface (HDMI) or a Digital Visual Interface (DVI) connection. For example, audio and video router 126 may be connected to OR hub 140 through one or more of an HDMI connection, a DVI connection, or a Universal Serial Bus (USB) connection. In some embodiments, audio and video router 126 can be configured to provide audio and video routing and/or teleconferencing functionality. Based on instructions from OR hub 140, audio and video router 126 can be configured to select and route media data (e.g., audio, images, and/or videos) from one or more endoscope cameras 130 to be displayed by touch panel 124 or another display. Therefore, images and live video may be displayed to medical practitioners (e.g., a surgeon) during a surgical procedure.

In some embodiments, OR hub 140 can be coupled to a hospital network 102 to enable authorized users to access or interact with devices external to operating room 120. In some embodiments, hospital network 102 can include a Local Area Network (LAN) and/or a wireless LAN (WLAN). Such devices external to operating room 120 may be referred to as networked devices (i.e., connected to hospital network 102) and may include a plurality of medical device data systems (MDDS). In some embodiments, the MDDS refers to hardware or software functions that are intended to transfer, store, convert formats, and/or display medical device data or medical imaging data. For example, the MDDS may include medical image storage devices such as imaging server 106. In some embodiments, imaging server 106 can be a server configured to store patient images or videos captured by medical devices such as endoscope camera 130 in operating room 120. For example, imaging server 106 may be a Digital Imaging and Communications in Medicine (DICOM) server that communicates with OR hub 140 via a TCP connection. In another example, the MDDS may include a data server 104 for storing patient data collected at or entered in operating room 120. For example, data server 104 may include an Electronic Health Record (EHR) system for storing the patient's data. In some embodiments, data server 104 can be a Secure File Transfer Protocol (SFTP) server configured to communicate with OR hub 200 through an SFTP connection set up over a TCP connection (e.g., on TCP port 22).

In some embodiments, network infrastructure 110 coupled to hospital network 102 enables OR hub 140 to communicate with networked devices such as data server 104 and imaging server 106. In some embodiments, network infrastructure 110 can include a Domain Name Service (DNS) server 116, a Dynamic Host Configuration Protocol (DHCP) server 112, and a Network Time Protocol (NTP) server 114, each of which provide functionality that are well understood by those skilled in the art. For example, DHCP server 112 may be a network server that automatically provides and assigns IP addresses and other network parameters to devices connected to hospital network 102 to enable such devices to communicate with each other. For example, DNS server 116 may associate information with domain names assigned to devices coupled to hospital network 102 to enable ease of configuring network connections. For example, DNS server 116 may maintain a directory of domain names and associated IP addresses to translate between a specific domain name and its associated IP address.

In some embodiments, NTP server 114 can be configured to provide clock synchronization functions for networked devices and OR hub 140 connected to hospital network 102. In particular, NTP server 114 may acquire time from an external source, maintain the acquired time in an internal local clock, and supply the maintained time to hospital network 102 using the network time protocol. Maintaining an accurate and synchronized time within operating room 120 may be an important security objective to ensure that the one or more medical devices operate accurately and that patient information is recorded accurately.

In some embodiments, to control, operate, and secure operation of the one or more devices connected to OR hub 140, OR hub 140 can include the following components: an operations user interface (UI) 142, system software 144, a firewall 146, software functions 147, security functions 148, and communication interfaces 149. Some functionality of each of these components will be described below. Each of these components are described in greater detail with respect to FIG. 2.

In some embodiments, communication interfaces 149 can include a plurality of interfaces (e.g., ports) that enable OR hub 140 to couple to and establish communication channels with a plurality of medical devices using one or more protocols from a plurality of preauthorized communication protocols. For example, communication interfaces 149 may include a plurality of USB ports to establish communication channels between OR hub 140 and one or more of printer 122, touch panel 124, and audio and video router 126. For example, communication interfaces 149 may include serial ports such as RS232 ports to establish communication channels between OR hub 140 and one or more of surgical lights 128, insufflator 132, and endoscope camera 130. For example, communication interfaces 149 may include HDMI or DVI ports to permit media communications between OR hub 140 and audio and video router 126.

In some embodiments, communication interfaces 149 can include one or more network interfaces that enable OR hub 140 to communicate with one or more networked devices over hospital network 102. For example, a network interface may include an Ethernet port that couples OR hub 140 to network infrastructure 110, imaging server 106, or data server 104.

In some embodiments, communication interfaces 149 are provisioned by a hub software developer to include a plurality of preauthorized interfaces that implement a plurality of preauthorized communication protocols. Therefore, authorized users that operate OR hub 140 may be restricted to operating devices (e.g., medical devices or networked devices) compatible with at least one of the preauthorized interfaces and that implement at least one of the preauthorized communication protocols. In some embodiments, these preauthorized interfaces and communication protocols are selected by the hub software developer to meet security standards and to strengthen the security posture of devices in operating room 120.

In some embodiments, system software 144 can be configured to manage and control hardware resources (e.g., memory, computing processes, and communication interfaces 149) to operate or execute software functions 147 from application software installed on OR hub 140, security functions 148 accessible from OR hub 140, and firewall 146. By running one or more of software functions 147, system software 144 can enable one or more medical devices in operating room 120 to be operated by authorized users as well as to enable the authorized users to access or interact with networked devices of hospital network 102. As described above, the one or more medical devices and networked devices can be operated from OR hub 140 through the communication channels established by communication interfaces 149 of OR hub 140.

In some embodiments, system software 144 can be configured to be accessible through operations UI 142. In some embodiments, operations UI 142 can be configured to be the only interface between users and system software 144 of OR hub 140. Accordingly, OR hub 140 can be configured to prevent users from directly accessing the underlying functions and system files of system software 144 and from accessing application software providing software functions 147. In some embodiments, system software 144 can include an Operating System such as a Windows Operating System that has been preconfigured by the hub software developer to meet certain security objectives (e.g., Microsoft Windows 10 Security baseline).

In some embodiments, operations UI 142 can be operated by users through touch panel 124, which may include a touchpad tablet, a mounted monitor, or a display. In some embodiments, operations UI 142 can be operated through voice commands processed by a speech recognizer residing in OR hub 140. In some embodiments, to improve the security posture of operating room 120, speech recognizer functionality is disabled. In other embodiments, the speech recognizer functionality can be configured to be disabled by default and can be accessible to users if expressly enabled by a user having an administrator credential, as will be further described below. In some embodiments, operations UI 142 can be operated through voice commands processed by a speech recognizer residing in audio and video router 126. For example, audio and video router 126 may detect, via a microphone, user speech commands and route the processed speech commands to OR hub 140 to operate operations UI 142. Example graphical user interfaces that operations UI 142 provides to users are shown and described below with respect to FIGS. 3-10.

In some embodiments, operations UI 142 can be configured to "lock" OR hub 140 such that a user cannot access or operate the one or more medical devices coupled to OR hub 140 in operating room 120 until that user is authenticated by operations UI 142. For example, operations UI 142 may present a login prompt that requests the user to enter a username and a password, which system software 144 may use to authenticate the user and determine which type of credential the authenticated user possesses.

In some embodiments, operations UI 142 can be configured to permit an authenticated user that has an operator credential to access medical-related functionality provided through OR hub 140. In some embodiments, users that have the operator credential may include medical practitioners such as surgeons, doctors, nurses, or physical assistants that interact with patients in a hospital. In some embodiments, the medical-related functionality can include access to one or more devices (e.g., medical devices or a networked device) connected to OR hub 140 as well as a set of software functions 147 installed on OR hub 140 to operate the one or more devices. In some embodiments, one of software functions 147 may include starting a patient case, entering patient information, capturing images or videos of a patient during a surgical procedure, or retrieving or storing patient data from or to a networked server. For example, one of software functions 147 may include transmitting and storing medical images or videos to imaging server 106 (e.g., a Picture Archiving and Communication System (PACS) server). In another example, one of software functions 147 may include transmitting and storing patient information to data server 104, which may be an SFTP server.

In some embodiments, operations UI 142 can be configured to permit an authenticated user that has an administrator credential to access the medical-related functionality (e.g., software functions 147) accessible through OR hub 140, security and administrative functionality provided by security functions 148 installed on OR hub 140, and access to configuration functions to set up OR hub 140. Therefore, the user having an authenticated administrator credential has the same access rights as users with the operator credential and has extended security and administrative rights not accessible by the users with the operator credential. In some embodiments, users that have the administrator credential may include a system administrator, an Information Technology (IT) administrator, a hospital network administrator, etc.

In some embodiments, security functions 148 can be provided by one or more security applications preloaded on OR hub 140 to detect and/or secure OR hub 140 against specific types of threat vectors. For example, security functions 148 may include anti-virus scanning, disk encryption, disabling and enabling ports, access control, or viewing audit logs or whitelisting logs. Other examples are further described below with respect to FIG. 2.

In some embodiments, the configuration functions can include configuring one or more settings of security functions 148, software functions 147, or firewall 146. For example, one or more network settings can be configured to establish a communication channel between OR hub 140 and a medical device. In another example, one or more server settings can be configured to allow OR hub 140 to communicate with a networked device such as imaging server 106 or data server 104. Other configuration functions may include configuring export options, shipment repair processing, language, or date/time. For example, audit logs or patient case files may be exported through preconfigured and preauthorized network connections.

In some embodiments, firewall 146 can be configured to secure data communications (i.e., both inbound and outbound communications) between OR hub 140 and one or more medical devices in operating room 120 as well as between OR hub 140 and networked devices through hospital network 102. In some embodiments, firewall 146 can be a software application controlled by system software 144. In other embodiments, firewall 146 can be a component of system software 144. In some embodiments, firewall 146 is configured to operate a permit-by-exception policy (also referred to as deny-by-default policy) to allow only connections that are preconfigured to establish communication channels with permitted devices (e.g., a medical device in OR hub or a networked device external to operating room 120) using preauthorized data communication protocols.

In some embodiments, firewall 146 can be configured to require the administrator to configure and individually enable or disable each incoming and outgoing network connection to OR hub 200 to strengthen the security posture of OR hub 200. In some embodiments, the specific connection between OR hub 140 and a permitted device may be configured by an authorized user through operations UI 142. For example, the authorized user may be a hospital network administrator authenticated as having an administrator credential. In contrast, non-administrative users such as medical practitioners may activate preapproved and preconfigured communication mechanisms that are set up by the administrator to transfer data on or off OR hub 200. In some embodiments, local connections to medical devices in operating room 120 can also be enabled or disabled by the administrator.

Figure 2:
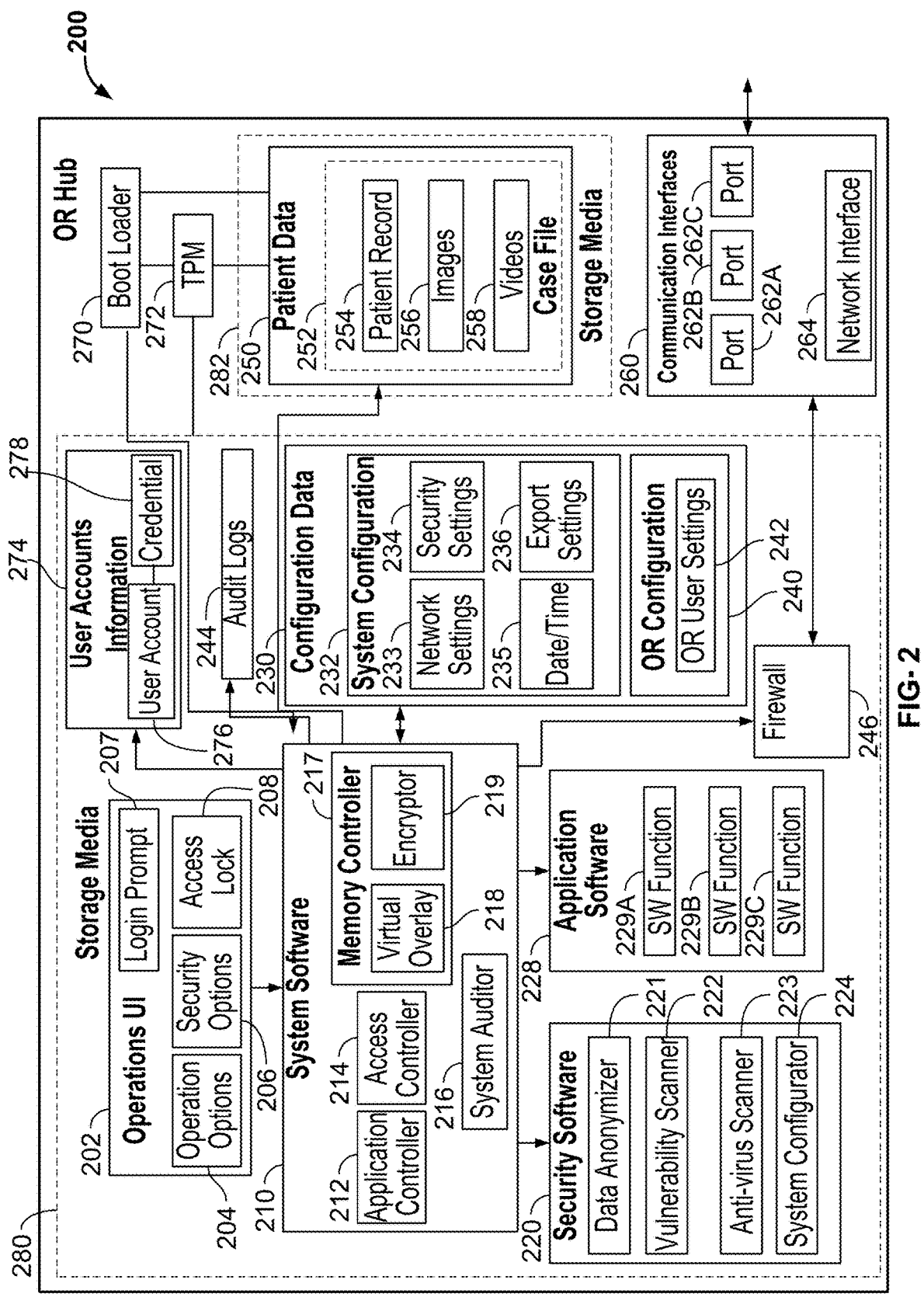
FIG. 2 illustrates components of an OR hub, according to some embodiments.

FIG. 2 illustrates components of an OR hub 200, according to some embodiments. OR hub 200 may be an example implementation of OR hub 140, as described above with respect to FIG. 1. In some embodiments, operations of OR hub 200 is controlled by system software 210. System software 210 can include an Operating System (OS).

In some embodiments, OR hub 200 includes an operations UI 202 that enables a user to interact with system software 210 to operate devices and OR hub 200 in operating room 120 according to a plurality of permitted software functions 229A-C or a plurality of security functions of security software 220 supplied to the user based on a type of user credential possessed by that user. Therefore, operations UI 202 presents a limited interface through which authorized users can access system software 210 to operate one or more coupled devices or OR hub 200 using preauthorized and preconfigured functions. In some embodiments, operations UI 202 implements role-based security that presents different types of device and function access privileges to users depending on the user credential that the users possess.

In some embodiments, operations UI 202 includes access lock 208 that prevents the user from operating and interacting with OR hub 200 and its connected devices (e.g., one or more medical devices or one or more networked devices) until that user is authenticated by operations UI 202. In some embodiments, operations UI 202 may provide login prompt 207 to the user and request that the user enter their user account credentials. For example, the user may be prompted to enter a username (or user ID) and a password. As will be further explained below, system software 210 may compare the user input with user accounts information 274 to determine whether to authenticate the user as well as to determine which type of user credential the user possesses. In some embodiments, user accounts information 274 can be one or more encrypted files that store user accounts 276 and their associated credentials 278.

In some embodiments, an operator credential can be assigned to users that are medical practitioners to permit them to access medical or patient related functionality provided by OR hub 200. For example, operations UI 202 may present the user having the operator credential with operation options 204 that correspond to authorized software functions 229A-C of application software 228. In some embodiments, operation options 204 are presented as a plurality of graphical elements within a panel or a screen provided by operations UI 202 to the user. Such graphical elements may include, for example, radio buttons, icons, text boxes, etc.

In some embodiments, software functions 229A-C includes functionality to access or operate a medical device in operating room 120, a networked device, or OR hub 200, or to access patient data 250 stored on storage media 282. For example, one of software functions 229A-C may include starting a case file for a patient, entering patient information in the case file, capturing images or video using endoscope camera 130 during a surgical procedure, or saving the case file to a preconfigured storage or imaging server 106.

In some embodiments, patient data 250 may be stored as case files 252 for each patient. In some embodiments, case file 252 may include patient record 254 of the patient as well as data generated during a surgical procedure of the patient such as images 256 or videos 258. For example, case file 252 may include notes or annotations added by medical practitioners (via operations UI 202) during a surgical procedure. Therefore, patient data 250 may contain protected health information (PHI) and/or personally identifiable information (PII).

In some embodiments, patient data 250 is stored and secured locally on OR hub 200. As will be further described below, the medical personnel may be permitted to export or transmit patient data 250 to the preconfigured storage via a preconfigured and preauthorized network connection.

In some embodiments, software functions 229A-C may include enabling the medical practitioner to set OR configurations 240 stored in configuration data 230. For example, medical practitioner may enter user settings 242 according to his or her preferences. These user settings 242 (also referred to as a surgeon profile) may include, for example, default settings of one or more medical devices in operating room 120. In some embodiments, OR configurations 240 are not sensitive information and are not encrypted. Additional examples of functionality are described below with respect to FIGS. 3 and 4.

In some embodiments, an administrator credential can be assigned to users that are hospital network administrators to permit them to access security and administrative related functionality provided by OR hub 200 in addition to access to the medical or patient related functionality provided to users assigned the operator credential. For example, operations UI 202 may present the user having an administrator credential with (i) operation options 204 corresponding to software functions 229A-C of application software 228, and with (ii) security options 206 that correspond to security related functions of security software 220. In some embodiments, security options 206 are presented as a plurality of graphical elements within a panel or a screen provided by operations UI 202 to the user. For example, the security related functionality may include running one or more security applications or configuring one or more system configurations 232, as will be further described below. Additional examples of functionality are described below with respect to FIGS. 5-10.

In some embodiments, to control and secure operations of devices coupled to OR hub 200, system software 210 can include the following components: an access controller 214, an application controller 212, a system auditor 216, and a memory controller 217. As described above with respect to FIG. 1, system software 210 can include an operating system that manages hardware resources (e.g., memory, communication interfaces 260, and computing processes or tasks) and execution of software on OR hub 200. For example, system software 210 may launch and control execution of security software 220 and application software 228 as well as permit users and running software to interface with stored data (e.g., configuration data 230 or patient data 250). In some embodiments, the operating system may include software that is part of a system image that is preconfigured by a hub software developer to comply with certain security objectives such as specific security standards or legal regulations.

In some embodiments, access controller 214 can be configured to control whether users have access to one or more security functions provided by security software 220, one or more software functions 229A-C provided by application software 228, a combination thereof, or neither based on user credentials possessed by the users. In some embodiments, access controller 214 can be configured to control which of the one or more security functions and which of the one or more software functions 229A-C are accessible to the user based on the user credential. For example, access controller 214 may operate in tandem with operations UI 202 to provide certain operation options 204 and certain security options 206 to an authenticated user.

In some embodiments, access controller 214 can be configured to authenticate a user based on user inputs (e.g., a username or ID and password) received from the user through login prompt 207 provided by operations UI 202. For example, access controller 214 may compare the received user inputs with data stored in user accounts information 274 to determine whether the user is authenticated and what type of credential the user possesses. In some embodiments, access controller 214 can identify an existing user account 276 corresponding to the user inputs and determine the associated user credential 278. As described above, the types of user credentials allowed on OR hub 200 may include an operator credential and an administrator credential.

In some embodiments, access controller 214 can permit an administrator with the administrator credential to manage creation of unique user accounts 276 stored in user accounts information 274. In some embodiments, access controller 214 can enforce password criteria during creation of user accounts 276 such that an associated password for a user account is strong and meets certain security standards. Therefore, user accounts information 274 cannot be accessed unless the user is authenticated to possess an administrator credential (i.e., is an authenticated administrator).

In some embodiments, access controller 214 can be configured to access an Active Directory of a hospital to allow the administrator more granular control of permitted user accounts 276 and their assigned user credentials 278. In some embodiments, user accounts 276 may be mapped to the Active Directory such that only designated individuals in the Active Directory are assigned user credentials 278 that allow them to operate OR hub 200.

In some embodiments, access controller 214 can be configured to initiate an auto logoff procedure if archived patient data is being displayed by operations UI 202 and no user interactions are detected by operations UI 202 in a predefined time interval (e.g., 5 minutes, 15 minutes, or 30 minutes, etc.). In some embodiments, access controller 214 can be configured to allow users to stay logged in during a surgical procedure.

In some embodiments, application controller 212 can be configured to control which executables (i.e., sometimes referred to as executable file, executable code, or an executable program) are authorized to be run by system software 210. In some embodiments, running an executable causes OR hub 200 to perform indicated tasks according to encoded instructions of the executable. For example, the executables may include one or more files of security software 220 or application software 228 preloaded on OR hub 200. In some embodiments, application controller 212 can block the execution of any executable not explicitly authorized.

In some embodiments, application controller 212 can be configured to manage a whitelist of authorized executables (also referred to as application whitelisting) that are checked to determine whether to permit an executable to be run by system software 210. In some embodiments, application controller 212 can also control which authorized changes or updates are to be made to software of OR hub 200. Accordingly, application controller 212 may prevent unauthorized programs or code such as worms, viruses, spyware, and malware that install themselves onto OR hub 200 from executing illegitimately. In some embodiments, the whitelist can be configured and preloaded to system software 210 by the hub software developer and cannot be disabled or edited by users with the operator credential or the administrator credential. Therefore, application controller 212 may maintain pre-defined baseline configurations of loaded software on OR hub 200 such as system software 210, security software 220, application software 228, or a combination thereof. In some embodiments, modifications to the whitelist can be introduced by the hub software developer through reloading software packages of system software 210 with a new or updated version. In some embodiments, only the hub software developer having a developer credential may initiate and cause OR hub 200 to update its software such as system software 210, as will be further described below.

In some embodiments, application controller 212 can be configured to perform application whitelisting on one or more programs or functions from a removable media (e.g., a USB device) connected to OR hub 200 if a media port (e.g., the USB port) of the OR hub 200 is enabled by an administrator. By checking whether an executable from the connected removable media is part of the whitelist, application controller 212 may prevent the removable media interface from being exploited.

In some embodiments, system software 210 may include a commercial operating system that includes a plurality of executables that may not meet required security standards. In these embodiments, the use of application controller 212 can prevent these unsecure executables (which are not part of the whitelist) from running.

In some embodiments, application controller 212 can also support memory control functions to prevent whitelisted applications from being exploited via memory buffer overflow attacks. For example, application controller 212 may prevent any unauthorized program that is on disk or injected into memory from executing and prevents unauthorized changes to an authorized baseline and thus protects from malicious attempts to hijack the system. In some embodiments, application controller 212 can trap and halt any detected unauthorized code injected into a running process.

In some embodiments, access controller 214 can be configured to control how system updates are to be applied to OR hub 200. In particular, access controller 214 may require a complete reload of system software 210 and/or security software 220 and application software 228 when updates are to be applied. This reload process may strengthen the security posture of OR hub 200 by maintaining a known system state and limits the need for the administrator to test individual patches or updates to system software. In some embodiments, user accounts information 274 and configuration data 230 may be retained across system updates.

In some embodiments, system auditor 216 can be configured to track and log a plurality of events on OR hub 200 to audit logs 244. In some embodiments, audit logs 244 include metadata gathered or generated by system software 210. In some embodiments, audit logs 244 can include audit user logs that are generated based on user interactions with operations UI 202, e.g., to control system software 210 to access one or more software functions 229A-C or one or more security functions of security software 220. For example, the plurality of logged events may include login or logoff operations performed by access controller 214 or include operator actions like access to certain configuration data 230 or patient data 250 (e.g., case file 252). A logged event may also include a change to one or more of system configurations 232 such as a network or server setting change. In some embodiments, a logged event may include a usage of software functions such as image or video capture or data export to an external media storage or an external device, as described below with respect to FIGS. 3, 4, and 8. In some embodiments, the usage of software functions may include one or more of the functionalities provided by OR hub 200 as described below with respect to FIGS. 3-10. For example, logged events may include an update to a device setting (e.g., a printer, surgical lights, OR hub 200), an update to a network setting (e.g., configured DICOM or SFTP server connection), an update to an active directory (e.g., a new or deleted operator account), a selection of a video source, a message saved by an operator, etc.

In some embodiments, each logged event may be associated with or include metadata that describe how or by whom the event was generated. For example, the metadata may include one or more of the following: a log time (e.g., a UTC time), a system time (e.g., an OS time with time zone), an event type, a serial number of an OR hub that generated the event, an OR hub part number, an OR hub MAC ID, a customer ID, a sales representative ID, a source of the event, an outcome, an operator ID of an operator that caused the event to be generated, an operator username of the operator that caused the event to be generated, or an operator message input by the operator that generated the event.

In some embodiments, audit logs 244 can include log files generated by security software 220 such as including scan results from vulnerability scanner 222 or anti-virus scanner 223.

In some embodiments, audit logs 244 can include whitelisting audit logs that are generated based on events of application controller 212. For example, these events may include information related to which executable files (e.g., a software function or program) was blocked by application controller 212. In other words, the whitelisting audit logs may include information related to which executable files were attempted to be run that were not permitted (i.e., not whitelisted) by application controller 212.

In some embodiments, audit logs 244 can include one or more encrypted files whose access is controlled by access controller 214 based on a user credential of a user operating OR hub 200 through operations UI 202. In other embodiments, audit logs 244 may be stored on unencrypted files. In some embodiments, as will be further described below with respect to FIG. 8, access controller 214 can permit an administrator (i.e., an authenticated user possessing an administrator credential) to navigate security options 206 provided by operations UI 202 to access and review audit logs 244. In some embodiments, security options 206 of operations UI 202 may provide the administrator with functionality to manage export of audit logs 244 to one or more destinations. For example, system auditor 216 may be configured by the administrator to perform automatic export of audit logs 244 on a periodic basis through a secure data communication protocol such as SFTP. In another example, system auditor 216 may enable the administrator to initiate on-demand export of audit logs 244 to a destination device such as to an external device via a USB connection.

In some embodiments, memory controller 217 can be configured to protect storage media 280 and 282 and secure data stored on storage media 280 and 282. To do so, memory controller 217 can include encrypter 219 and can implement virtual overlay 218.

In some embodiments, virtual overlay 218 protects physical storage media 280 and 282 from repeated data writes. In particular, memory controller 217 can intercept data writes to a protected storage volume (e.g., one of storage media 280 and 282 or one or more designated portions of storage media 280 and 282) and direct the data writes to virtual overlay 218. In some embodiments, the use of virtual overlay 218 improves reliability and stability of OR hub 200 by reducing wear on write-sensitive media such as solid-state drives.

In some embodiments, memory controller 217 can be configured to protect system software 210 from unintentional or unauthorized changes by reverting any changes to default settings (e.g., default settings stored in configuration data 230) upon shutdown of OR hub 200.

In some embodiments, encrypter 219 can be configured to encrypt patient data 250 stored on storage media 282 using one or more preconfigured cryptographic algorithms (e.g., AES-256 bit with FIPS 140-2 validation). In some embodiments, encrypter 219 may encrypt patient data 250 by case file 252 such that un-encrypted patient information is accessible to an authorized user only through operations UI 202. For example, operation options 204 may present the authorized user with a permitted software function to view patient record 254 in case file 252. Once the permitted software function is initiated, encrypter 219 may decrypt the patient data 250 to enable the authorized user to view the unencrypted patient record 254.

In some embodiments, security software 220 provide the security related functions accessible by an administrator through security options 206 of operations UI 202. In some embodiments, the security related functions may be provided by a data anonymizer 221, a vulnerability scanner 222, an anti-virus scanner 223, and a system configurator 224. In some embodiments, operation and statuses of one or more executed security functions may be stored in audit logs 244.

In some embodiments, data anonymizer 227 can be configured to anonymize patient data 250 stored in storage media 282 of OR hub 200 based on a password (or key) supplied by an administrator. In some embodiments, this data anonymization functionality may be desired by the administrator when OR hub 200 needs to be transported to the hub software developer to be serviced and repaired. In these situations, patient data 250 needs to be protected from unauthorized parties such as non-medical personnel to comply with legal regulations (e.g., the Health Insurance Portability and Accountability Act data security requirements). In some embodiments, once OR hub 200 has been serviced by the hub software developer and returned to the administrator, the administrator may supply data anonymizer 227 with the same password to enable data anonymizer 227 to deanonymize patient data 250 such as patient records 254. Once deanonymized, patient data 250 may be accessed by medical personnel through operation options 204 of operations UI 202.

In some embodiments, vulnerability scanner 222 can be configured to enable the administrator to provision a temporary network connection to a remote scanning platform (e.g., Qualys Vulnerability Management or Tenable Nessus) to detect whether any vulnerabilities are present in OR hub 200 such as present in system software 210, security software 220, or application software 228. Therefore, vulnerability scanner 222 may facilitate a vulnerability scanner external to OR hub 200 to connect to and run on OR hub 200 based on user inputs received by operations UI 202, such as selected security options 206. In some embodiments, if a vulnerability above a threshold severity level (e.g., level 3) is detected, system software 210 may be configured to request the administrator to patch the vulnerability. In some embodiments, vulnerability scanner 222 may cause scan results such as an identified vulnerability or a threshold severity level to be stored in audit logs 244 or transmitted to a hub software developer. In some embodiments, once a hub software developer is notified of the vulnerability via, for example, receipt of audit logs 244, the developer may create a vulnerability patch to be applied to OR hub 200. In some embodiments, as described above, access controller 214 can be configured to permit the vulnerability patch to be downloaded to and applied as a software update to OR hub 200.

In some embodiments, vulnerability scanner 222 can provision a credential scan of OR hub 200 by temporarily creating a user account 276 having an administrator credential and configuring firewall 246 to allow a preconfigured network connection between OR hub and the remote scanning platform. For example, the preconfigured network connection may include one or more rules that specify a host address and port of the remote scanning platform, one of ports 262A-C, and a secure network protocol for data communications across the network connection. In some embodiments, once the credential scan is provisioned, the remote scanning platform may access and scan files on OR hub 200 to detect vulnerabilities. In some embodiments, the temporarily provisioned credential scan, including the temporary user account, may be removed upon restart of OR hub 200. In some embodiments, once the credential scan is provisioned, operations UI 202 may prevent normal operation of OR hub 200 until the scan completes or OR hub 200 is rebooted.

In some embodiments, once a vulnerability scan is initiated by vulnerability scanner 222, access controller 214 can control operations UI 202 to execute access lock 208 of OR hub 200. For example, access lock 208 may block use of operations UI 202 with a popover screen while scanning is in progress. In some embodiments, the administrator may be permitted to cancel the scan through a selection of a cancel option in the popover screen. This cancelation functionality provided to the user enables OR hub 200 to exit scanning mode and enter operation mode to permit immediate use of OR hub 200 in emergency situations. Upon cancelling or completing the scan, system software 210 may be configured to reboot OR hub 200 to bring OR hub 200 to a last best configuration.

In some embodiments, anti-virus scanner 223 can be configured to scan files on storage media 280 and/or storage media 282 to determine whether an infected file is present on OR hub 200. For example, anti-virus scanner 223 may scan files of application software 228, security software 220, and/or system software 210. In some embodiments, in response to detecting the infected file, anti-virus scanner 223 can instruct system software 210 (e.g., access controller 214) to shut down OR hub 200.

In some embodiments, anti-virus scanner 223 can be configured to be initiated by the administrator to perform full system scanning when OR hub 200 is in a non-operative mode to prevent negatively impacting a performance of OR hub 200 during a surgical procedure. In the non-operative mode, operations UI 202 may prevent users from accessing operation options 204 to control or use one or more medical devices in operating room 120.

In some embodiments, anti-virus scanner 223 can be configured to be manually initiated by a user to scan a removable media (e.g., a USB device) if the media port (e.g., the USB port) is enabled by the administrator. In some embodiments, anti-virus scanner 223 can be configured to automatically scan the removable media upon insertion into communication interfaces 260. If malware is detected on the removable media, system software 210 may block the communication channel between OR hub 200 and the removable media.

In some embodiments, system software 210 can store a status indicating that the infected file was detected. During start-up of OR hub 200, boot loader 270 can be configured to check whether the status is present, according to some embodiments. If the status is present, boot loader 270 may cause an alert indicating the status to be displayed by operations UI 202 and cause system software 210 to shut down OR hub 200. In effect, once an infected file has been detected, system software 210 locks OR hub 200 and prevents users from operating and interacting with OR hub 200. In some embodiments, OR hub 200 may need to be physically transported to a hub software developer who will repair OR hub 200.

In some embodiments, system configurator 224 enables a medical practitioner having the operator credential to be provided by operation options 204 to set OR configuration 240 such as use settings 242 in a surgeon profile, as described above.

In some embodiments, system configurator 224 enables an administrator having the administrator credential to be provided with security options 206 to set system configurations 232 such as network settings 233, security settings 234, date/time settings 235, and export settings 236.

In some embodiments, network settings 233 may include which of ports 262A-C are enabled or disabled as well as configurations for an authorized network connection using a permitted communication protocol selected from a plurality of permitted communication protocols. Network settings 233 may also include server settings of a networked device (e.g., setting a DICOM server or an SFTP server). In some embodiments, export settings 236 may specify how selected patient data 250 can be exported to a remote storage.

As described above, the administrator may configure network settings to control which data transfer mechanisms are available to and can be activated by authorized medical practitioners. However, administrators themselves are restricted in the types of network connections that are permitted and the types of data communication protocols that are permitted via operations UI 202. In some embodiments, the plurality of supported and permitted protocols are provisioned by the hub software developer and may be modified only by users with the developer credential. For example, as discussed above, the developer credential may be information (e.g., a security key) input into OR hub 200 by the hub software developer that permits the hub software developer to access rights and functions not accessible to the administrator or medical practitioner.

In some embodiments, the developer credential may be stored on a removable storage media (e.g., a USB drive or an external drive) that is coupled to OR hub 200 via, for example, one of ports 262A-C (e.g., a USB port). In these embodiments, access controller 214 can be configured to receive and verify the developer credential from the removable storage media. In some embodiments, once access controller 214 authenticates the developer credential, access controller 214 permits the hub software developer to access or change system software 210, including low level access to an Operating System of system software 210.

In some embodiments, when the removable storage media is coupled to OR hub 200, the removable storage media can serve as an interface to permit an authorized hub software developer to gain access to or change system software 210. For example, the removable storage media may include software that prompts the hub software developer to input developer credential. In some embodiments, once the software verifies the developer credential, OR hub 200 permits the authenticated hub software developer to access system software 210 directly. For example, the software can cause system software 210 (e.g., access controller 214) to enable system services to be accessible to the authenticated hub software developer. Such system services may include system management or access tools such as a task manager (e.g., a Windows Task manager), a control panel or a command line interface (e.g., Windows PowerShell or a command prompt). These system services may enable the hub software developer to gain low level access to the Operating System of system software 210. In some embodiments, the authenticated hub software developer may be permitted such access for as long as the removable storage media is connected to OR hub 200. If the connection is disrupted or the removable storage media is disconnected, OR hub 200 may be configured to re-disable user access to the system services.

In some embodiments, before allowing software on the removable storage media to run, OR hub 200 can run one or more security functions (e.g., security functions 148) of security software 220 to verify that the connected removable storage media is safe. For example, OR hub 200 may run anti-virus scanner 223 to verify that the removable storage media does not contain malware.

In some embodiments, security settings 234 may include configuring settings of one or more security functions of security software 220. For example, security settings 234 may include when anti-virus scanner 223 is run, whether USB ports are enabled or disabled, how often or when audit logs 244 are to be exported, etc.

In some embodiments, date/time settings 235 are security sensitive information that may be set only by administrators having the administrator credential. As will be further described below with respect to FIGS. 9A-B, date/time settings 235 may include a time zone, a date format, or settings to synch date/time settings 235 to an NTP server.

In some embodiments, OR hub 200 can be configured to maintain three versions of configuration files storing configuration data 230. These three versions may include a first configuration file of default settings, a second configuration file of last best settings, and a third configuration file of current settings. If any corrupted files are detected on system files, system software 210 may reconfigure OR hub 200 to use the default settings or the last best settings to prevent software running on OR hub 200 to use corrupted files.

In some embodiments, OR hub 140 includes a Trusted Platform Module (TPM) 272 that stores one or more cryptographic keys used for hardware encryption and decryption of storage media 280 and 282 on OR hub 200. In some embodiments, the one or more cryptographic keys are unique and specific to OR hub 140 and TPM 272 prevents these cryptographic keys from being extracted. In some embodiments, the one or more cryptographic keys enables full disk encryption of one or more storage media 280 and 282 residing on OR hub 200. In some embodiments, TPM 272 can be configured to encrypt storage media 282 storing patient data 250 such that patient data remains secure when OR hub 200 is offline or exposed to unauthorized parties. For example, hard drive encryption of storage media 280 and 282 may ensure that stored data are permanently inaccessible when storage media 280 or 282 are physically removed from OR hub 200.

In some embodiments, OR hub 200 includes a boot loader 270 (e.g., a BIOS) that is configured to initiate a start-up process of OR hub 200 when OR hub 200 is powered on. In some embodiments, boot loader 270 can be configured to check that storage media 280 storing system software 210 is encrypted and that storage media 282 storing patient data 250 is encrypted before completing startup of OR hub 200. In some embodiments, in response to detecting that storage media 280 is properly encrypted, boot loader 270 can be configured to mount (i.e., decrypt and load) system software 210, security software 220, and application software 228 based on one or more cryptographic keys stored in a Trusted Platform Module (TPM) 272. In some embodiments, as part of mounting software, boot loader 270 may verify signatures of each mounted software (e.g., system software 210, security software 220, or application software 228) to ensure only permitted and untampered software is being mounted. If any signature cannot be verified, boot loader 270 may be configured to shut off OR hub 200. Once system software 210 has been successfully mounted, boot loader 270 can be configured to unlock (i.e., decrypt) storage media 282 based on the one or more cryptographic keys to enable authenticated users to access decrypted patient data 250.

In some embodiments, boot loader 270 is secured and inaccessible to medical personnel such as users having the operator credential or the administrator credential. In some embodiments, boot loader 270 may be accessible to the hub software developer having the developer credential received by and verified by OR hub 200. For example, boot loader 270 may store a BIOS password that protects its software. In some embodiments, during or prior to start-up, the hub software developer may input the developer credential that is verified against the BIOS password by boot loader 270. If the developer credential matches the stored BIOS password, boot loader 270 may permit the hub software developer to gain access or modify the software run by boot loader 270.

In some embodiments, if boot loader 270 detects that storage media 280 and 282 are not encrypted, operations UI 202 may be disabled from being presented to users to prevent users from operating OR hub 200. In some embodiments, an administrator may need to reinstall system software 210 to re-encrypt storage media 280 and 282.

In some embodiments, by providing multiple storage media 280 and 282 secured through TPM 272, OR hub 200 is less likely to be exploited when left unattended or is being shipped from one location to another. In some embodiments, the one or more cryptographic keys are retrieved and temporarily stored within a secure key store of system software 210 once OR hub has booted up. During memory operations, system software 210 can be configured to write data to storage media 282 using the cryptographic keys to implement hardware encryption. These cryptographic keys may be wiped from system software 210 when OR hub 200 shuts down.

In some embodiments, OR hub 200 includes communication interfaces 260 that enables OR hub 200 to couple to and establish communication channels with one or more medical devices and one or more networked devices. In some embodiments, communication interfaces 260 include a plurality of ports 262A-C and network interface 264. In some embodiments, ports 262A-C may include one or more serial ports (e.g., RS232 ports), one or more USB ports, one or more HDMI ports, one or more DVI ports, one or more Ethernet (RJ-45) ports, one or more audio ports, or a combination thereof. In some embodiments, network interface 264 may include a network interface controller (NIC), which may enable a wired connection (e.g., through the Ethernet port) and, possibly, a wireless connection (e.g., Wi-Fi) to a local area network such as hospital network 102.

In some embodiments, firewall 246 can be configured to control data communications to and from OR hub 200 through communication interfaces 260. In some embodiments, firewall 246 may be a software application executed by system software 210. In other embodiments, firewall 246 may be a component of system software 210.

In some embodiments, firewall 246 can be configured to control which network connections are permitted and which communication protocols are permitted to operate on each of the interfaces (e.g., ports 262A-C and network interface 264). For example, if network interface 264 includes a wireless interface (e.g., including an antenna to enable wireless communications), firewall 246 may be configured to permit wireless data communications that employ one of a plurality of preselected protocols. For example, the plurality of preselected protocols may include WEP Open, WPA/WPA2-PSK TKIP/AES, or WPA/WPA2 Enterprise TKIP/AES protocol. Therefore, firewall 246 may permit connections only to pre-configured network ports and protocols. In some embodiments, to improve the security posture of OR hub 200, firewall 246 can be configured to permit only connections to wired interfaces and disable connections to wireless interfaces such as a WiFi protocol. In some embodiments, firewall 246 can be preconfigured to not allow wireless connections to strengthen the security posture of OR hub 200.

In some embodiments, firewall 246 may automatically configure ports 262A-C or network interface 264 based on network settings 233 configured by the administrator without notifying the user. As noted above, hospital personnel may be limited to interfacing with OR hub 200 through operations UI 202 and not directly with firewall 246.

Accordingly, firewall 246 may block incoming network connections that are not permitted and preconfigured by the administrator. Additionally, firewall 246 may prevent medical personnel (e.g., a user with the operator credential) from creating outgoing network connections except through a predefined protocol and a preconfigured destination as set by the administrator.

In some embodiments, firewall 246 may permit a preconfigured external connection (e.g., an SFTP or a DICOM connection) to a networked device (outside of operating room 120) to be active if the connection is being actively used by a logged in user. In some embodiments, once the external connection has been configured, the external connection remains open and permits users to access the pre-configured external connection. In other embodiments, once an initiated information transfer completes, firewall 246 may be configured to close the external connection.

FIGS. 3-10 illustrate example screens that show how an operations UI (e.g., operations UI 202) provided by an OR hub (e.g., OR hub 200) permits a user that possesses an appropriate user credential to access permitted (i.e., preapproved) software functions to operate devices (e.g., medical devices or networked devices) in an operating room, access permitted security functions, and/or configure user access privileges, security settings, and/or networking settings. In some embodiments, the OR hub includes or is coupled to a touch screen (e.g., touch panel 124) that enables users to interact with the operations UI through a touch interface by tapping on displayed icons to select the icons. In some embodiments, for displayed fields that require text entry, the operations UI may control the touch screen to display a digital keyboard to be operated by the user. For ease of explanation, FIGS. 3-10 will be described below with respect to the elements of FIGS. 1 and 2. Additionally, a user that is authenticated by operations UI 202 to possess an operator credential will be referred to as a medical practitioner (e.g., a surgeon or a nurse) and a user that is authenticated by operations UI 202 to possess an administrator credential will be referred to as an administrator (e.g., hospital network administrator or a systems admin).

Figure 3:
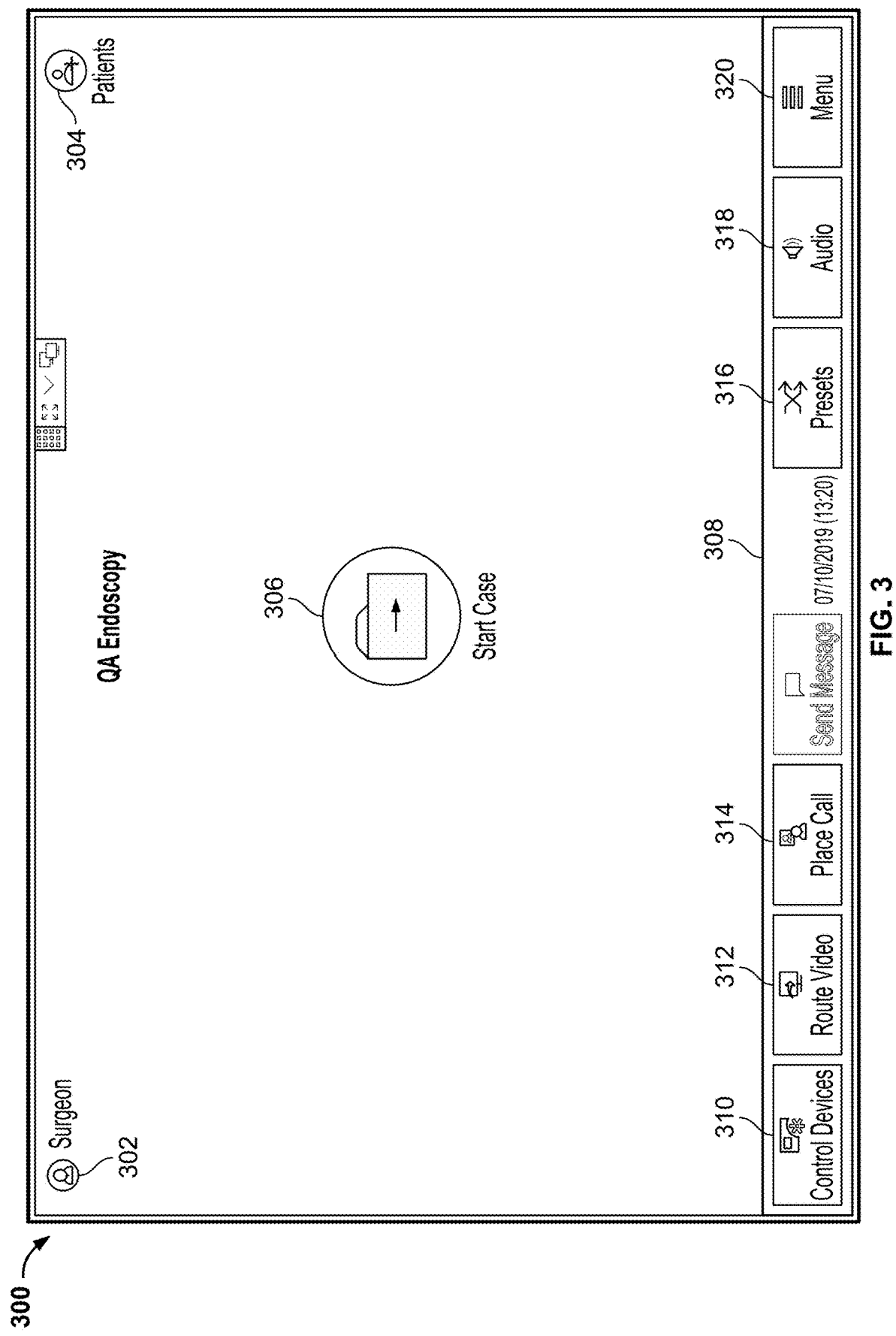
FIG. 3 is an example screen that illustrates how an operations user interface (UI) of an OR hub permits a user having an operator credential to operate devices in an operating room, according to some embodiments.

FIG. 3 is an example screen 300 that illustrates how operations UI 202 of OR hub 200 permits a user (e.g., a medical practitioner) having an operator credential to operate devices in an operating room 120, according to some embodiments. As described with respect to FIG. 1, such a user can be a medical practitioner such as a surgeon, a nurse practitioner, or a physician assistant, etc. In some embodiments, after authenticating a user as having the operator credential, operations UI 202 can present the authenticated user with a screen as shown in screen 300.

Screen 300 can be a home screen that provides the user with links to software functions 229A-C permitted by OR hub 200 to enable the user to interact with one or more medical devices and/or one or more networked devices. In some embodiments, operations UI 202 can generate screen 300 showing a plurality of graphical elements such as a user profile icon 302, a patient icon 304, a start case icon, and a taskbar 308. In some embodiments, when user profile icon 302 is selected, operations UI 202 enables the user to select a user profile created locally on the OR hub. For example, the user profile may be stored in OR configurations 240. Once the user profile is selected, operations UI 202 displays a name corresponding to the selected user profile (e.g., a surgeon's name) next to the user profile icon 302. When patient icon 304 is selected operations UI 202 enables the user to view a list of patients to select from, add a new patient, or enter patient information. In some embodiments, operations UI 202 retrieves the patient related information from patient data 250. When start case icon 306 is selected, operations UI 202 starts a case workflow for the surgical procedure being conducted on the patient.

In some embodiments, taskbar 308 displays a plurality of graphical elements (e.g., icons or buttons) corresponding to a plurality of permitted software functions 229A-C accessible to the user. One of the graphical elements may include a control devices icon 310 that, when selected, enables the user to configure or operate the medical devices within operating room 120. Another graphical element may include a route video icon 312, that when selected, enables the user to route a connected video input (e.g., from endoscope camera 130) to a selected output such as a connected display, a codec, or a recording device. Another graphical element may include a place call icon 314, that when selected, enables the user to make audio and/or video calls to other medical practitioners (e.g., another surgeon or a pathology lab) or to broadcast audio and/or video for training purposes. Another graphical element may include a presets icon 316 to enable the user to preconfigure personalized user settings 242 based on a procedure type. For example, these settings may include a room lighting level and set up of cameras or audio/video routes. Another graphical element may include an audio icon 318, that when selected, enables the user to control an audio volume and timbre (e.g., a bass, treble, and balance of audio and/or OR hub volume). In some embodiments, taskbar 308 may also display a current data and time.

In some embodiments, when menu options 320 of taskbar 308 is selected, operations UI 202 displays a panel to permit the user to access a help menu, archive a patient case, log off, restart OR hub 200, or power off the OR hub 200.

Figure 4:
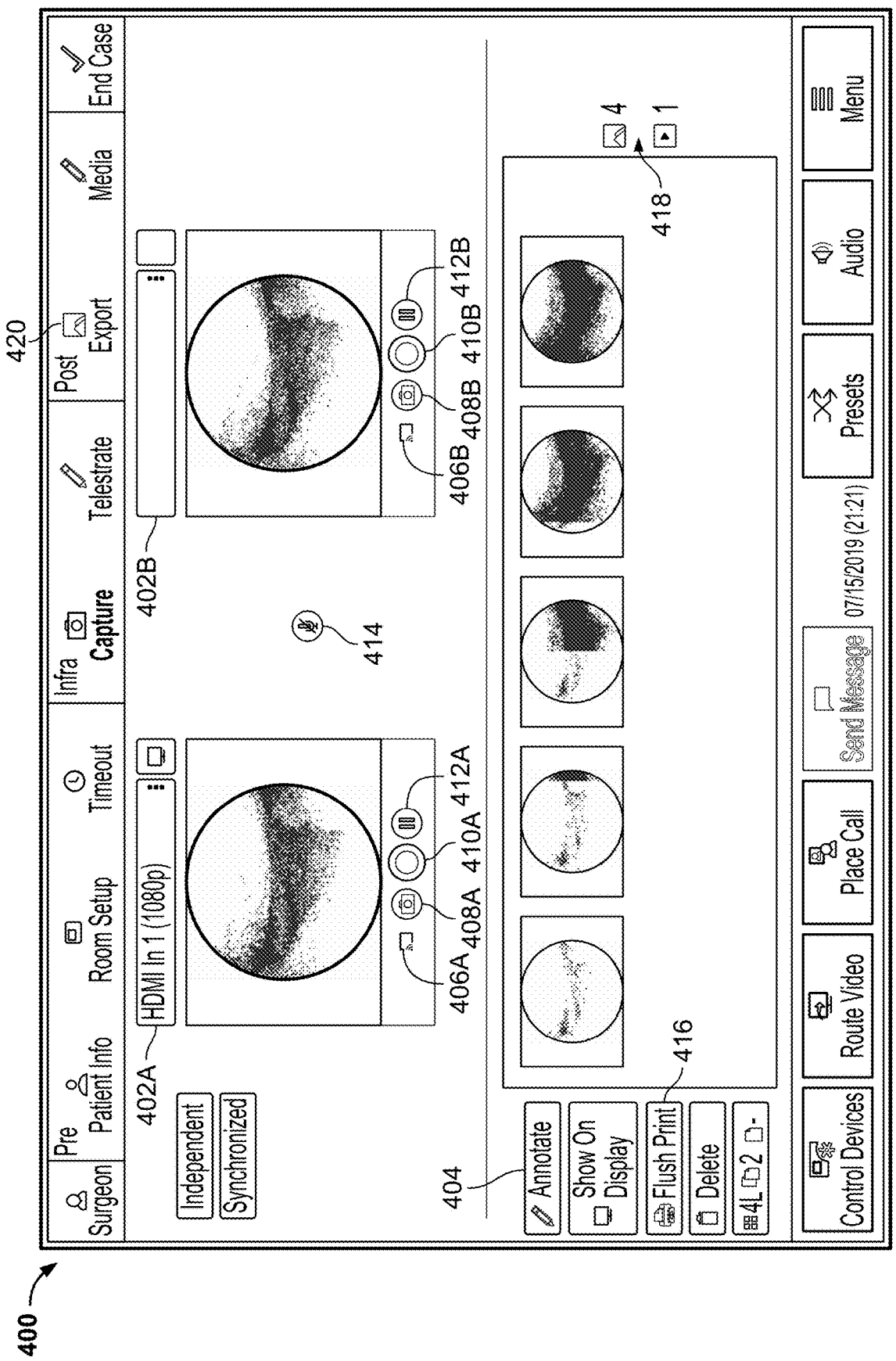
FIG. 4 is an example screen that illustrates how an operations UI of an OR hub permits a user having an operator credential to operate imaging devices in an operating room, according to some embodiments.

FIG. 4 is an example screen that illustrates how operations UI 202 of OR hub 200 permits the user having the operator credential to operate imaging devices in operating room 120, according to some embodiments. As noted above, such a user is a medical practitioner. In some embodiments, operations UI 202 provides the user with a plurality of graphical elements that link to software functions 229A-C permitted by OR hub 200 to permit the user to control one or more video sources 402A-B based on imaging devices such as endoscope camera 130 connected to OR hub 200. Each of these graphical elements and their associated software function is described below.

In some embodiments, selection of annotation button 404 causes operations UI 202 to display patient case information as well as the user to enter notes to the patient case file.

In some embodiments, in a multi-camera mode, operations UI 202 permits the user to operate a plurality of selected video sources 402A-B in a synchronized mode (where one set of controls commands multiple video sources 402A-B) or in an independent mode (where each of video source 402A-B may be independently controlled). In some embodiments, streaming options 406A-B for video sources 402A-B may be disabled. Alternatively, the user may be enabled to select streaming options 406A-B to stream live video to a selected destination. In some embodiments, selecting microphone button 414 permits the user to mute or unmute audio recording.

In some embodiments, each of displayed video source 402A-B may be displayed with a plurality of graphical elements for camera operation. For example, such graphical elements may include a camera button 408A-B to capture an image, a record/stop button 410A-B to start/stop recording live video, or a pause button 412A-B to pause recording of respective video sources 402A-B.

In some embodiments, screen 400 shows a media gallery button 418 that enables the user to view images or videos captured by one or more of video sources 402A-B. For example, five images are shown in screen 400. In some embodiments, selecting print option 416 permits the user to print one or more selected images via a connected printer 122.

In some embodiments, screen 400 also provides an export icon 420 that enables the user to select one or more images or videos for export to a target destination. As described above with respect to FIG. 2, the user may be able to select from a plurality of export connections preconfigured by an administrator. For example, the user may be enabled to select a previously configured DICOM or SFTP connection. In some embodiments, archived patient case files (e.g., case file 252) may be exported by selection of an archived cases option through selection of menu options 320, as described above with respect to FIG. 3. In some embodiments, the user may be enabled to select a preconfigured DICOM or SFTP connection.

In some embodiments, FIGS. 5-10 show how operations UI 202 permits a user having an administrator credential to access security functions provided by security software 220 of OR hub 200. As noted above and for each reference, such a user may be referred to as an administrator.

Figure 5:
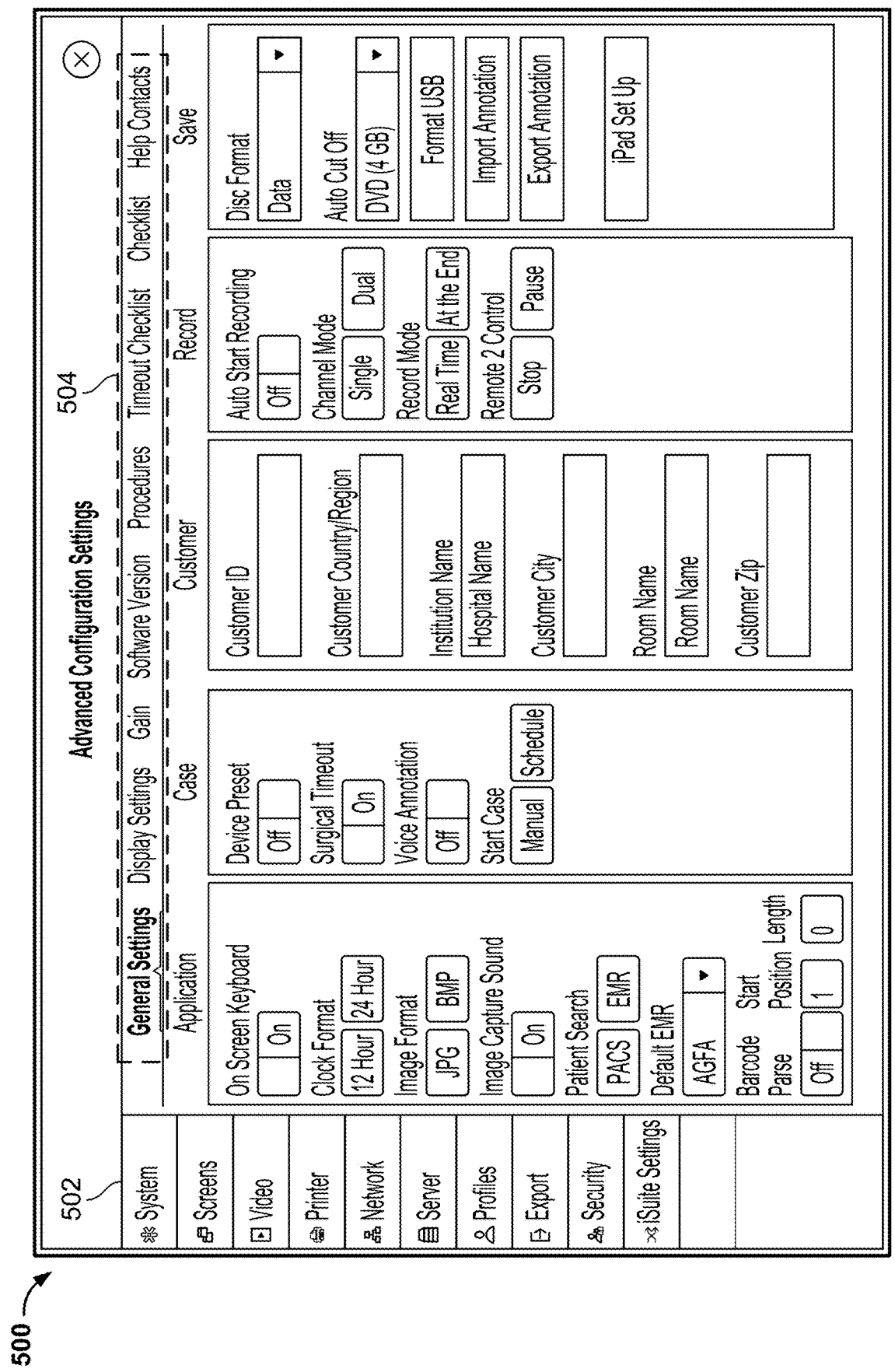
FIG. 5 is an example screen that illustrates how an operations UI of an OR hub permits a user having an administrator credential to set configurations for operating devices in an operating room, according to some embodiments.

FIG. 5 is an example screen 500 that illustrates how operations UI 202 of OR hub 200 permits a user having an administrator credential (i.e., an administrator) to set configurations for operating devices and OR hub 200 in an operating room, according to some embodiments. For example, these configurations may correspond to functionality provided by system configurator 224 of OR hub 200. In some embodiments, a subset of the functionality shown in screen 500 may be accessible to a medical practitioner through operation options 204 of operations UI 202.

Screen 500 shows a screen that includes a setting groups panel 502 that includes a plurality of tabs that, upon selection, permits the administrator to set specific settings for the entity corresponding to the selected tab. These groups may include system settings, screen settings, video settings, printer settings, network settings, server settings, profile settings, export settings, security settings, etc. As shown in screen 500, a video group may be selected and operations UI 202 may show settings options 504 corresponding to the selected group. For example, the administrator may be permitted to change system or video settings such as an image format for captured images (e.g. JPEG or BMP), whether voice annotation is permitted, whether auto recording or dual-channel recording is permitted, gain levels for various video inputs such as for HDMI or DVI, etc. In some embodiments, configurable settings may include display settings that the administrator can set to control when live video will time out, which statuses are shown on the display screen, as well as format resolution of output displays, etc.

Figure 6:
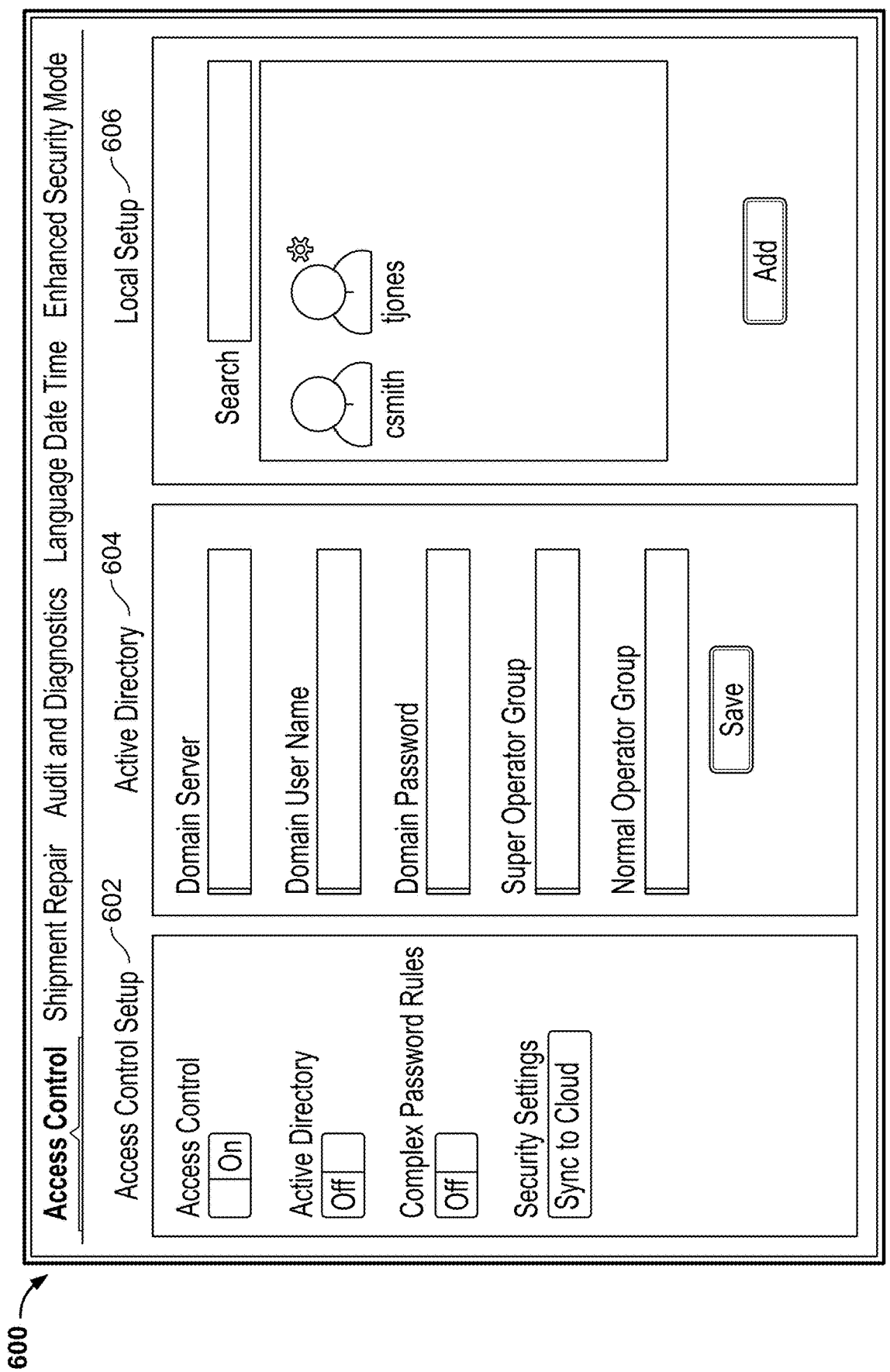
FIG. 6 is an example screen that illustrates how an operations UI of an OR hub permits a user having an administrator credential to control user access to the OR hub, according to some embodiments.

FIG. 6 is an example screen 600 that illustrates how operations UI 202 of OR hub 200 permits the user having an administrator credential (i.e., an administrator) to control user access to OR hub 200, according to some embodiments. Screen 600 shows a screen that may be presented to the administrator by operations UI 202 to enable the administrator to access the user access functions provided by access controller 214.

In some embodiments, operations UI 202 provides access control setup options 602 that enable the administrator to control settings such as security settings as well as whether active directory is enabled. In some embodiments, operations UI 202 disables synching user accounts information 274 to an active directory. In these embodiments and as shown, the active directory option remains disabled and cannot be changed by the administrator. When enabled, the administrator may enter parameters to access and synch to the active directory of the hospital.

In some embodiments, screen 600 includes a local setup panel 606 that enables the administrator to manage user accounts information 274. For example, the administrator may be permitted to add a user account by assigning user profile information (e.g., a username, a first name, and a last name), assigning an associated password, and assigning a user credential to the added user account (e.g., an operator credential or an administrator credential). The administrator may also change profile information of a currently added user account. As described above, locally created user accounts may be stored in user accounts information 274.

Figure 7:
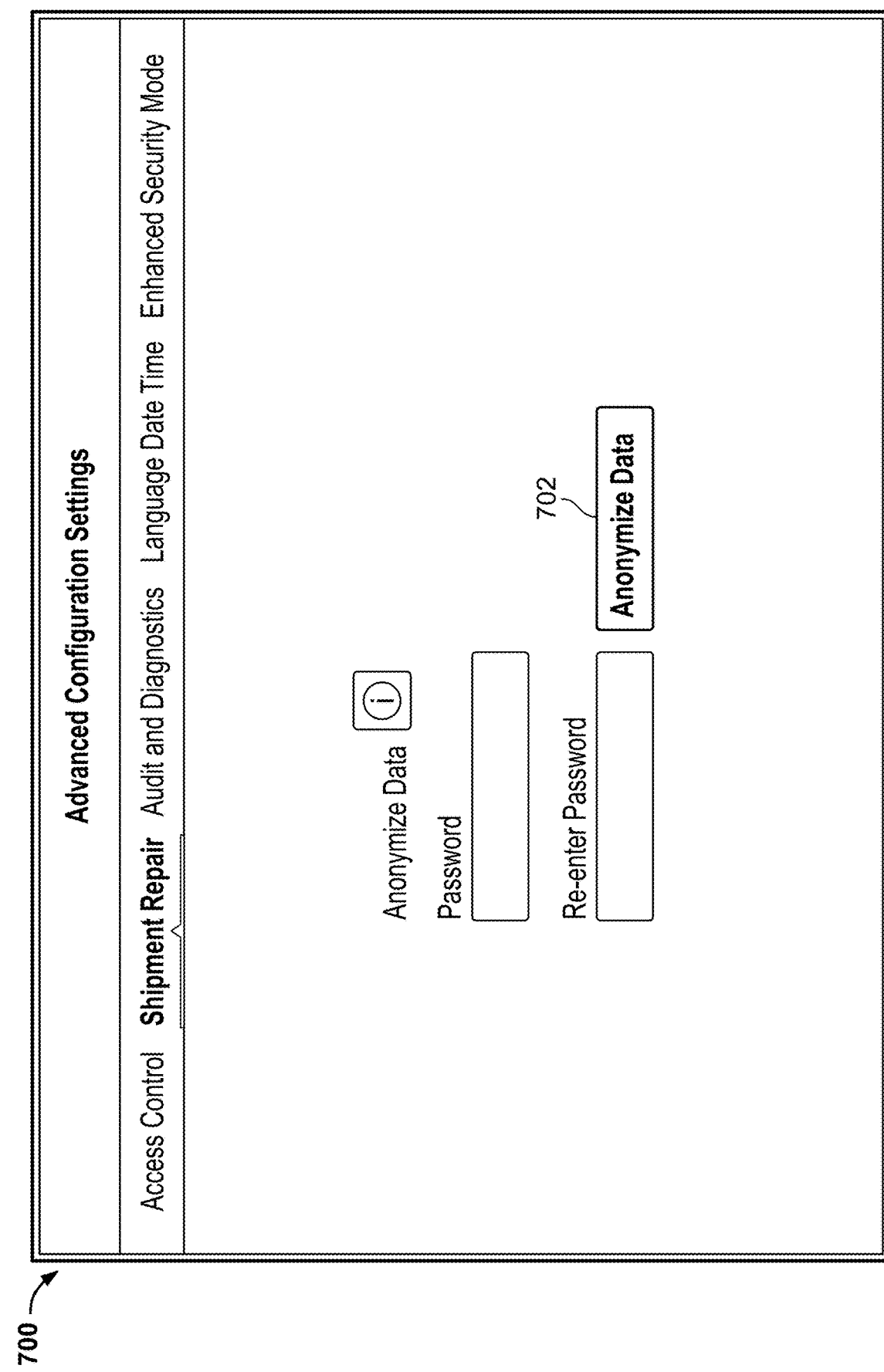
FIG. 7 is an example screen that illustrates how an operations UI of an OR hub permits a user having an administrator credential to anonymize user data stored on the OR hub prior to shipment, according to some embodiments.

FIG. 7 is an example screen 700 that illustrates how operations UI 202 of OR hub 200 permits a user having an administrator credential (i.e., an administrator) to anonymize user data stored on the OR hub prior to shipment, according to some embodiments. Screen 700 shows a screen that may be presented to the administrator by operations UI 202 to enable the administrator to access the data anonymize functions provided by data anonymizer 221. In particular, the administrator may be permitted to enter and confirm a password used by data anonymizer 221 to anonymize (e.g., encrypt) patient data 250 stored on OR hub 200. In some embodiments, selection of anonymize data button 702 by the administrator causes data anonymizer 221 to perform its function.

Figure 8:
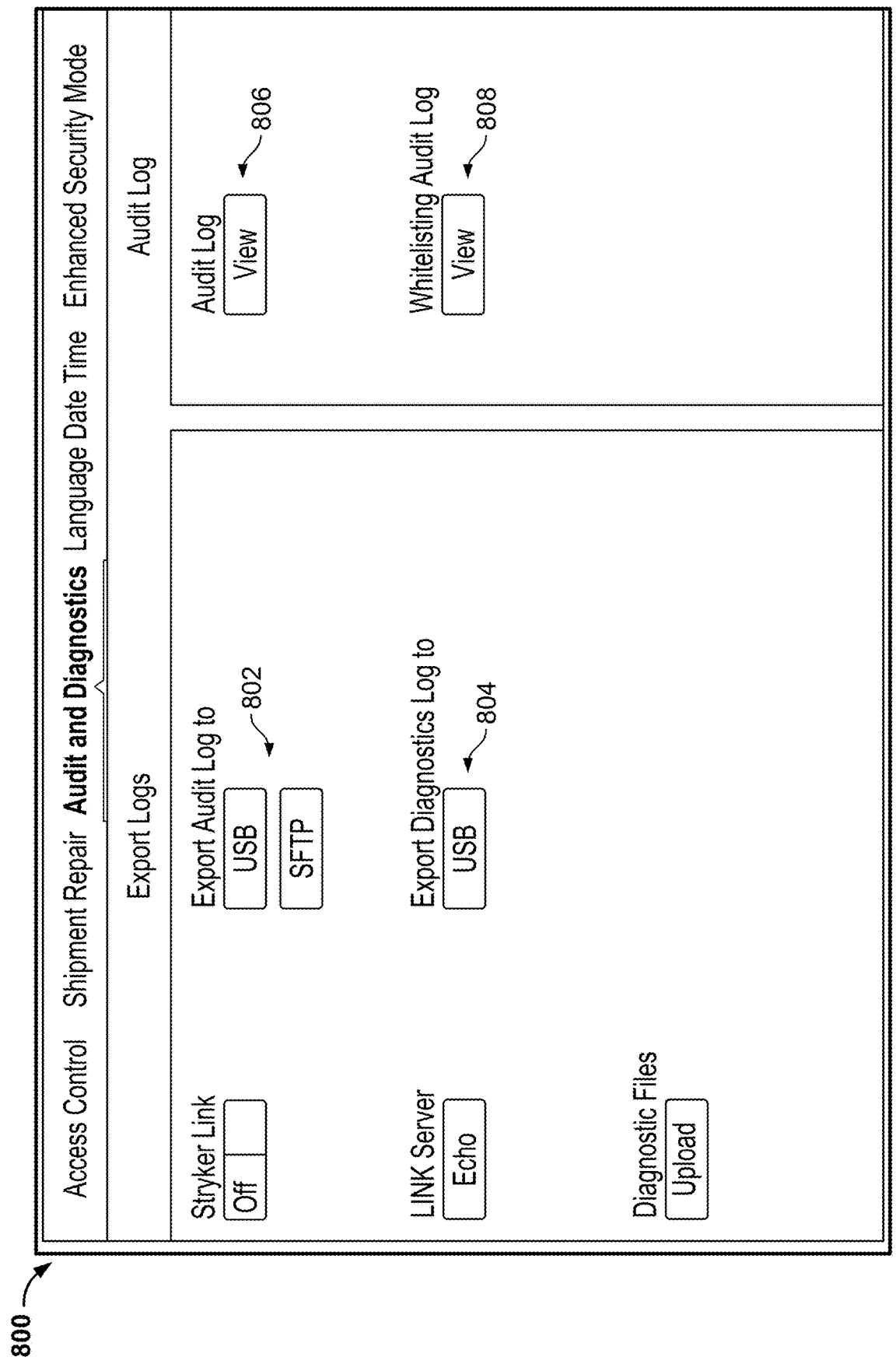
FIG. 8 is an example screen that illustrates how an operations UI of an OR hub permits a user having an administrator credential to view or export logs generated by the OR hub, according to some embodiments.

FIG. 8 is an example screen 800 that illustrates how operations UI 202 of OR hub 200 permits a user having an administrator credential (i.e., an administrator) to view or export logs generated by OR hub 200, according to some embodiments.

Screen 800 can be a screen that provides the administrator with links to security functions permitted by OR hub 200 and related to viewing or exporting audit logs 244. In some embodiments, operations UI 202 generates and provides screen 800 that includes a plurality of graphical elements to enable the administrator to interact with one or more medical devices and/or one or more networked devices. In some embodiments, operations UI 202 can generate screen 300 showing a plurality of graphical elements such as audit user log button 806 and a whitelisting audit log button 808, that when selected, enables the administrator to view the audit event logs and the whitelisting audit logs, respectively.

Screen 800 also shows audit log export options 802 and diagnostic log export option 804 that provides export functionality to the administrator. In some embodiments, operations UI 202 presents the administrator with one or more preauthorized communication protocols such as USB and SFTP in audit log export options 802. Once the USB option is selected by the administrator, system auditor 216 may be configured to export audit log 244 to a USB device via a USB port. If the SFTP option is selected, operations UI 202 may present the administrator with a screen to set parameters for the SFTP connection and when audit log 244 is to be exported. For example, the parameters may include whether to automatically export audit logs 244 every time OR hub 200 boots up, server address and port of a destination device for receiving audit logs 244, and a user name and password.

Figure 9A:

FIGS. 9A-B are example screens 900A-B that illustrate how operations UI 202 of OR hub 200 permits a user having an administrator credential (i.e., an administrator) to set a date and time of OR hub 200, according to some embodiments. As shown in FIG. 9A, operations UI 202 can provide the administrator with a screen 900A that includes a plurality of graphical elements to permit the administrator to set a language and date/time settings 235. As shown, the administrator may be permitted to set various time and date options. For example, the administrator may be permitted to change a time zone, a date format, or set a date and/or time.

In some embodiments, operations UI 202 permits the user to synch OR hub 200 using a network time protocol (NTP). Once selected as shown in region 902, operations UI 202 may present screen 900B to permit the administrator to set parameters for an NTP server such as an NTP server address and a port number.

Figure 10:
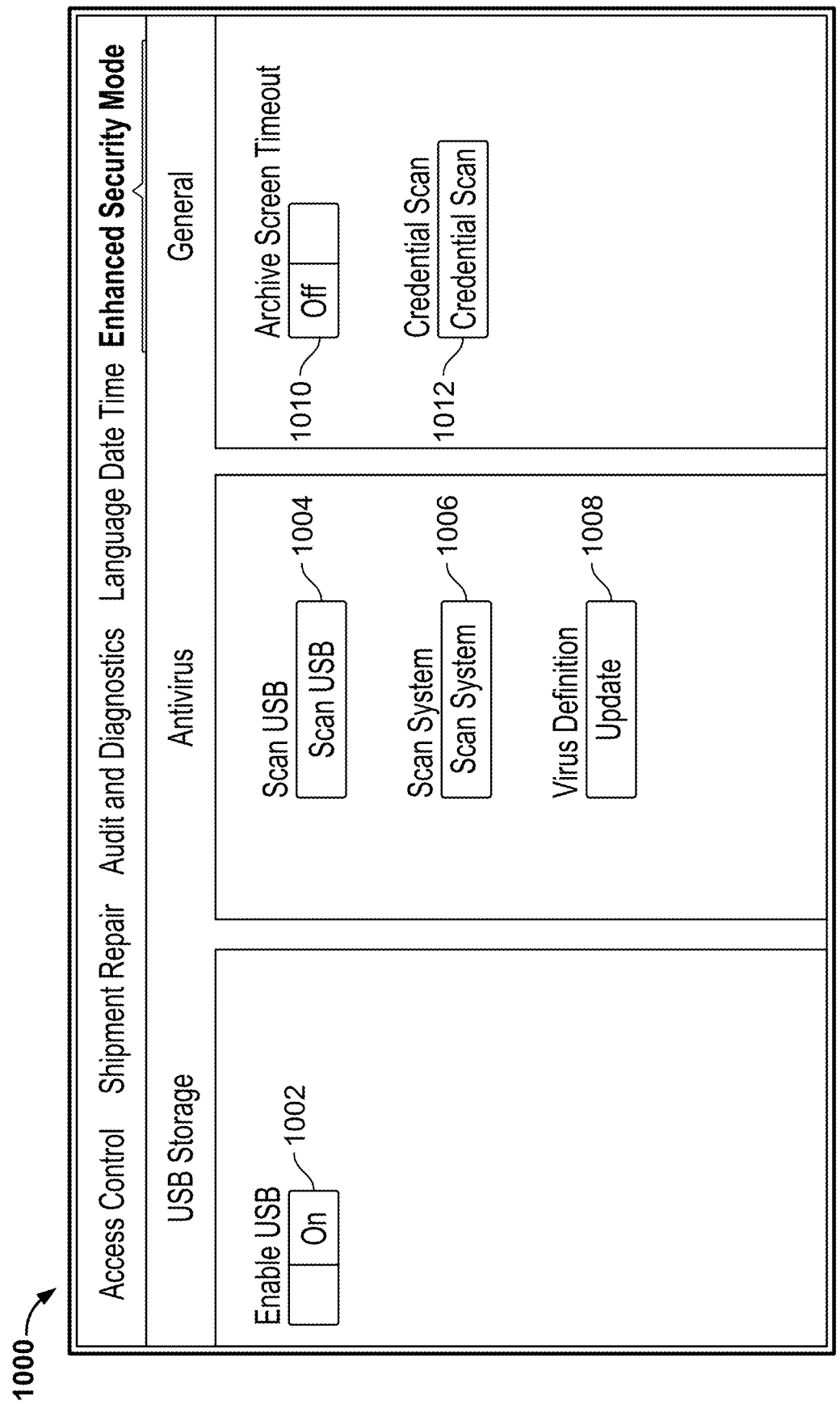
FIG. 10 is an example screen that illustrates how an operations UI of an OR hub permits a user having an administrator credential to access security functions provided by the OR hub, according to some embodiments.

FIG. 10 is an example screen 1000 that illustrates how operations UI 202 of OR hub 200 permits a user having the administrator credential (i.e., an administrator) to access security functions provided by OR hub 200, according to some embodiments. Screen 1000 can be a screen that provides the administrator with a plurality of graphical elements that when selected run a corresponding security function on security software 220 or system software 210. For example, selection of screen timeout 1010 enables the administrator to control whether a user is automatically logged out of operations UI 202 after a predetermined interval of inactivity.

In some embodiments, screen 1000 shows a toggle option 1002 that permits the administrator to enable or disable a USB port for connecting OR hub 200 to a USB storage device. Screen 1000 also shows a scan USB button 1004 that permits the administrator to initiate an anti-virus scan of a connected USB storage device.

In some embodiments, screen 1000 shows a scan system button 1006 that, when selected by the administrator, initiates vulnerability scanner 222 or anti-virus scanner 223 to perform a system scan of OR hub 200. During a system scan, OR hub 200 may disable USB connections to a USB storage device. As described above with respect to FIG. 2, if an infected file is detected during the system scan, operations UI 202 may be configured to display an alert indicating the detected, infected file and cause system software 210 to shut down OR hub 200. If any user attempts to reboot the shutdown OR hub 200, boot loader 270 may cause the alert to be reshown and may shut down OR hub 200 again.

In some embodiments, screen 1000 shows a virus definition update option 1008 that permits the administrator to initiate update of virus scan software. In some embodiments, the updated virus definition may be loaded on a removable storage device (e.g., a USB storage device) from which the updated virus definition is retrieved and used to update anti-virus scanner 223.

In some embodiments, screen 1000 shows a credential scan option 1012 that, when selected by the administrator, initiates a credential scan performed by vulnerability scanner 222. For example, the administrator may be prompted to enter a user name and password that grants administrator credential to a remote scanning platform. In some embodiments, after completing the credential scan, operations UI 202 may display a popup window that indicates a status of the scan and requires the administrator to reboot OR hub 200.

Figure 11:
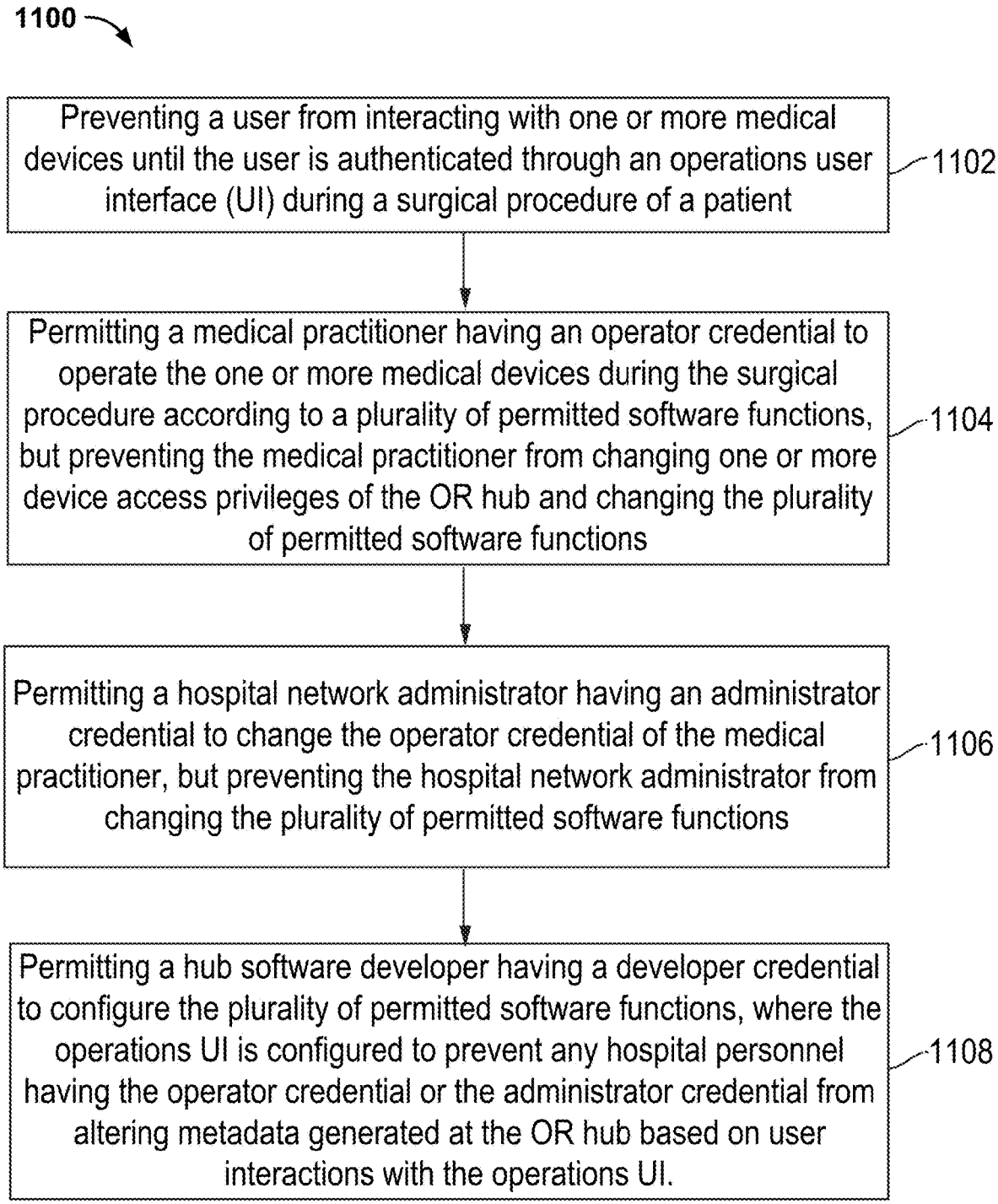
FIG. 11 is a flowchart illustrating a method for operating devices in an operating room, according to some embodiments.

FIG. 11 is a flowchart illustrating a method 1100 for operating devices in an operating room, according to some embodiments. Method 1100 may be implemented by an OR hub such as OR hub 140 or OR hub 200 as described above with respect to FIGS. 1 and 2, respectively. In some embodiments, a non-transitory computer readable storage medium stores one or more programs configured to be executed by one or more processors of the OR hub where the one or more programs include instructions for implementing any of the steps described below with respect to method 1100. For ease of illustration, one or more steps of method 1100 may be described below with respect to the components of OR hub 200 of FIG. 2 or devices of system 100 of FIG. 1.

In step 1102, the OR hub prevents a user from interacting with one or more medical devices until the user is authenticated though an operations UI (e.g., operations UI 202) during a surgical procedure of a patient. In some embodiments, the OR hub is coupled to the one or more medical devices in the operating room. For example, these medical devices may include surgical lights 128, printer 122, insufflator 132, endoscope camera 130, touch panel 124, and/or audio and video router 126.

In some embodiments, the OR hub runs system software (e.g., an operating system) that manages memory and processes on the OR hub, including software and hardware resources. In some embodiments, the OR hub can implement the operations UI to be an application that allows the user to interact with the system software according to permitted functionality accessible through the operations UI. In some embodiments, the permitted functionality is previously vetted and preloaded by a hub software developer into the OR hub. In some embodiments, the operations UI may serve as the only way for users to access and interact with the system software.

In step 1104, the operations UI of the OR hub permits a medical practitioner having an operator credential to operate the one or more medical devices during the surgical procedure according to a plurality of permitted software functions, but prevents the medical practitioner from changing one or more device access privileges of the OR hub and changing the plurality of permitted software functions. In some embodiments, the system software includes an access controller (e.g., access controller 214) that is configured to authenticate the medical practitioner as having the operator credential based on user inputs received through the operations UI (e.g., through login prompt 207). For example, the access controller may authenticate a user by comparing received user input with user accounts information (e.g., user accounts information 274) stored on the OR hub.

In some embodiments, the access controller can be configured to permit the medical practitioner to access the plurality of permitted software functions (e.g., provided by application software 228) through display of a plurality of graphical elements (e.g., provided by operation options 204) corresponding to the plurality of permitted software functions. In this way, the medical practitioner may only interact with the system software through the graphical elements represented by the operation options to access only the permitted software functions. Moreover, the operations UI does not present the medical practitioner with any options to change the permitted software functions, thereby preventing the medical practitioner from downloading, deleting, or changing application software preloaded on the OR hub. As described above with respect to FIGS. 2-4, the permitted software functions enable authorized users to operate a variety of medical devices or networked devices, and/or access or process patient data from the operating room.

In step 1106, the operations UI of the OR hub permits a hospital network administrator having an administrator credential to change the operator credential of the medical practitioner, but prevents the hospital network administrator from changing the plurality of permitted software functions. In some embodiments, the access controller can be configured to authenticate the hospital network administrator as having the administrator credential based on inputs received through the operations UI.

In some embodiments, the operations UI can be configured to display a panel (e.g., an arrangement of graphical elements for display) that provides the network administrator with the functionality of configuring user accounts and assigning associated user credentials. For example, the network administrator may be permitted to add a new user and assign an operator credential or an administrator credential to the new user. In another example, the network administrator may change or delete the operator credential of the medical practitioner. Like with the operation options presented to a medical practitioner, the operations UI does not present the network administrator with any options to change the permitted software functions, thereby preventing the network administrator from downloading, deleting, or changing the application software preconfigured on the OR hub.

In some embodiments, the operations UI can be configured to permit the network administrator to access the same permitted software functions (e.g., provided by application software 228) provided to medical practitioners as well as to access security functions (e.g., provided by security software 220) and configuration functions provided by the OR hub. As described above with respect to FIGS. 2 and 5-10, the permitted security and configuration functions may enable authorized users to, for example, run permitted security software programs, configure various data communication settings, and control user access to the OR hub.

In step 1108, the OR hub permits a hub software developer having a developer credential to configure the plurality of permitted software functions and where the operations UI is configured to prevent any hospital personnel (e.g., a medical practitioner or a network administrator) having the operator credential or the administrator credential from altering metadata generated at the OR hub based on user interaction with the operations UI. As described above with respect to FIG. 2, the developer credential may be information (e.g., a security key) that is inputted and verified by a removable storage media connected to the OR hub. Once the developer credential is verified, the removable storage media may cause the OR hub to enable the hub software developer to access system services provided by the system software of the OR hub.

In some embodiments, the OR hub permits the hub software developer with the developer credential to directly access the functions of a system software (e.g., an Operating System) of the OR hub. For example, these functions may include low level access to the system software. In some embodiments, the generated metadata can include audit logs and/or operation system logs as described above with respect to FIG. 2.

Figure 12:
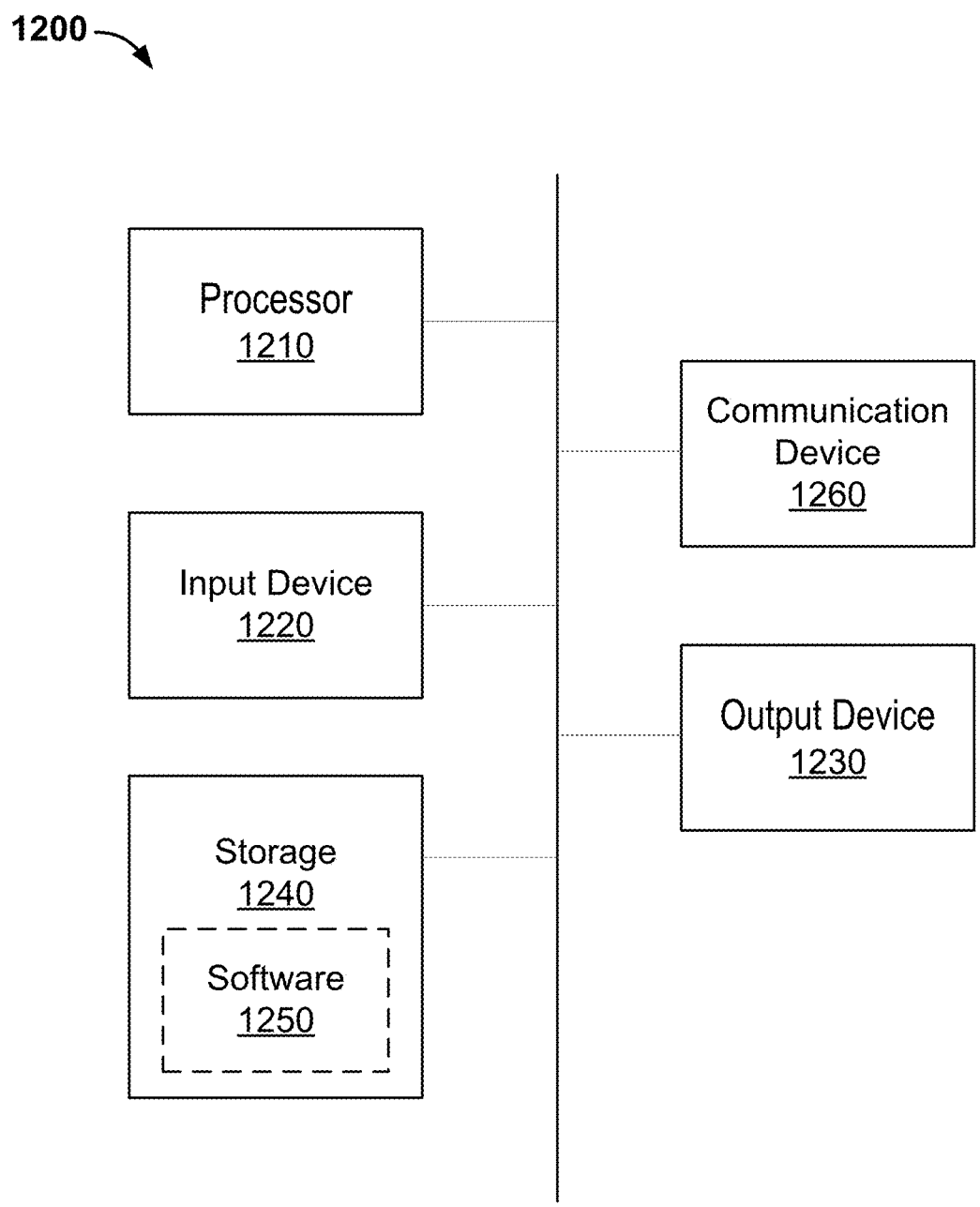
FIG. 12 illustrates an example of a computing device, according to some embodiments.

FIG. 12 illustrates an example of a computing device 1200, according to some embodiments. Device 1200 can be a host computing device connected to a network. For example, device 1200 may be an example implementation of one or more of the networked devices or OR hub 140, described above with respect to FIG. 1. Device 1200 can be a client computer or a server. As shown in FIG. 12, device 1200 can be any suitable type of microprocessor-based device, such as a personal computer, work station, or server. The device can include, for example, one or more of processor 1210, input device 1220, output device 1230, storage 1240, and communication device 1260. Input device 1220 and output device 1230 can generally correspond to those described above and can either be connectable or integrated with the computing device.

Input device 1220 can be any suitable device that provides input, such as a touchscreen, keyboard or keypad, mouse, or voice-recognition device. Output device 1230 can be any suitable device that provides output, such as a touchscreen, haptics device, or speaker.

Storage 1240 can be any suitable device that provides storage, such as an electrical, magnetic, or optical memory including a RAM, cache, hard drive, or removable storage disk. Communication device 1260 can include any suitable device capable of transmitting and receiving signals over a network, such as a network interface chip or device. The components of the computing device can be connected in any suitable manner, such as via a physical bus, or wirelessly.

Software 1250, which can be stored in storage 1240 and executed by processor 1210, can include, for example, the programming that embodies the functionality of the present disclosure (e.g., as embodied in the devices described above). For example, software 1250 may include system software (e.g., an operating system), application software, or security software.

Software 1250 can also be stored and/or transported within any non-transitory, computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1240, that can contain or store programming for use by or in connection with an instruction-execution system, apparatus, or device.

Software 1250 can also be propagated within any transport medium for use by or in connection with an instruction-execution system, apparatus, or device, such as those described above, that can fetch instructions associated with the software from the instruction-execution system, apparatus, or device and execute the instructions. In the context of this disclosure, a transport medium can be any medium that can communicate, propagate, or transport programming for use by or in connection with an instruction-execution system, apparatus, or device. The transport readable medium can include, but is not limited to, an electronic, magnetic, optical, electromagnetic, or infrared wired or wireless propagation medium.

Device 1200 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1200 can implement any operating system suitable for operating on the network. Software 1250 can be written in any suitable programming language, such as C, C++, Java, or Python. In various embodiments, application software embodying the functionality of the present disclosure can be deployed in different configurations, such as in a client/server arrangement, for example.

The foregoing description, for purpose of explanation, has made reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments, with various modifications, that are suited to the particular use contemplated.

Although the disclosure and examples have been fully described with reference to the accompanying figures, it is to be noted that various changes and modifications will be apparent to those skilled in the art. Such changes and modifications are to be understood as being included within the scope of the disclosure and examples as defined by the claims.

What is claimed is:

1. A method for improving cybersecurity of an operating room, comprising:
   at an operating room (OR) hub storing patient data and coupled to one or more medical devices in the operating room, the one or more medical devices comprising an imaging device:
      preventing a user from interacting with the imaging device until the user is authenticated through an operations user interface (UI) during a surgical procedure on a patient;
      permitting, via the operations UI, a medical practitioner having an operator credential to perform a plurality of permitted software functions comprising operating the imaging device via the OR hub to capture an image or video of the patient during the surgical procedure, storing the image or video of the patient in a case file, and transmitting at least a portion of the case file to an external device via a preconfigured network connection, but preventing the medical practitioner from changing one or more imaging device access privileges of the OR hub, changing the preconfigured network connection, and changing the plurality of permitted software functions;
      permitting, via the operations UI, a hospital network administrator having an administrator credential to change the operator credential of the medical practitioner, access audit logs comprising information related to usage of the permitted software functions including metadata generated at the OR hub based on user interactions with the operations UI, and change the preconfigured network connection, but preventing the hospital network administrator from changing the plurality of permitted software functions; and
      permitting a hub software developer having a developer credential to configure the plurality of permitted software functions, wherein the operations UI is configured to prevent any hospital personnel having the operator credential or the administrator credential from altering the metadata generated at the OR hub based on user interactions with the operations UI.

2. The method of claim 1, comprising:
running system software to operate a firewall on the OR hub to control inbound and outbound network connections to the operating room.

3. The method of claim 1, wherein the system software comprises an operating system of the OR hub.

4. The method of claim 2, wherein the system software is configured to allow the plurality of permitted software functions corresponding to the one or more medical devices to run on the OR hub.

5. The method of claim 2, comprising:
permitting, via the operations UI, the hospital network administrator having the administrator credential to select one of a plurality of permitted communication protocols to change the preconfigured network connection between the OR hub and the external device; and
automatically provisioning a firewall to allow the preconfigured network connection.

6. The method of claim 5, comprising:
permitting, via the operations UI, the medical practitioner having the operator credential to access the external device via the preconfigured network connection.

7. The method of claim 6, comprising:
enabling the preconfigured network connection when the medical practitioner is permitted to operate the imaging device during the surgical procedure; and
disabling the network connection to the networked device when the medical practitioner is logged out of the operations UI.

8. The method of claim 5, wherein changing the preconfigured network connection between the OR hub and the external device comprises:
prompting, via the operations UI, the hospital network administrator to select a network port of the OR hub and a device identifier of the external device.

9. The method of claim 1, wherein the external device comprises an SFTP server or a DICOM server.

10. The method of claim 1, wherein the one or more medical devices comprises surgical lights, an insufflator, an audio and video (AV) router, or a printer.

11. The method of claim 1, comprising:
permitting, via the operations UI, the medical practitioner having the operator credential to access patient data generated by the OR hub or the one or more medical devices during the surgical procedure.

12. The method of claim 1, comprising:
storing patient data on an encrypted memory of the OR hub, the patient data generated based on user interactions between the medical practitioner and the operations UI during the surgical procedure.

13. The method of claim 12, wherein the patient data comprises audio, video, or textual data generated by one or more permitted software functions of the permitted software functions accessed by the medical practitioner during the surgical procedure.

14. The method of claim 12, wherein the imaging device comprises an endoscope camera, and wherein the patient data comprises the image or video captured by the endoscope camera.

15. The method of claim 12, comprising:
permitting, via the operations UI, the hospital network administrator having the administrator credential to select one of a plurality of permitted communication protocols to change the preconfigured network connection between the OR hub and the external device; and
automatically provisioning the firewall to allow the preconfigured network connection.

16. The method of claim 15, comprising:
permitting, via the operations UI, the medical practitioner to select the external device for exporting the patient data outside of the operating room through the preconfigured network connection.

17. The method of claim 1, comprising:
permitting, via the operations UI, the hospital network administrator to individually enable or disable communication ports of the OR hub to control local connections between the OR hub and the one or more medical devices.

18. The method of claim 17, wherein the communication ports comprise a USB port or a serial port.

19. The method of claim 1, comprising:
restricting, via the operations UI, the medical practitioner having the operator credential from accessing the metadata generated at the OR hub; and
permitting, via the operations UI, the hospital network administrator having the administrator credential to view the metadata.

20. The method of claim 1, comprising:
coupling the OR hub to a touch panel; and
providing the operations user interface (UI) for display on the touch panel.

21. The method of claim 1, wherein permitting the medical practitioner to perform a plurality of permitted software functions comprises:
configuring settings of surgical lights, an endoscope camera, or an insufflator based on inputs of the medical practitioner received by the operations UI.

22. The method of claim 1, comprising:
permitting, by the operations UI, the hospital network administrator having the administrator credential to assign the operator credential to one or more other medical practitioners to allow the one or more other medical practitioners to operate the one or more medical devices and to access one or more preconfigured network connections during surgical procedures.

23. The method of claim 1, comprising:
preventing, via the operations UI, any hospital personnel from executing software functions other than one or more of the plurality of permitted software functions set by the hub software developer.

24. The method of claim 1, comprising:
permitting, via the operations UI, the hospital network administrator having the administrator credential to run one or more security functions from a plurality of permitted security functions installed on the OR hub.

25. The method of claim 24, wherein the one or more security functions comprise an anti-virus scanner, and wherein the method comprises:
precluding the anti-virus scanner from executing during the surgical procedure; and
permitting, via the operations UI, the hospital network administrator to initiate the anti-virus scanner to scan the OR hub during a non-operative mode of the OR hub.

26. The method of claim 1, wherein the developer credential comprises information inputted to a removable media storage.

27. The method of claim 26, comprising:
prompting the hub software developer to input the developer credential when the removable media storage is coupled to the OR hub; and
permitting the hub software developer to configure the plurality of permitted software functions upon verifying the developer credential.

28. An operating room (OR) hub for improving cybersecurity of an operating room, comprising:
one or more processors;
memory; and
one or more programs, wherein the one or more programs are stored in the memory and configured to be executed by the one or more processors, the one or more programs including instructions for:
preventing a user from interacting with an imaging device until the user is authenticated through an operations user interface (UI) during a surgical procedure on a patient;
permitting, via the operations UI, a medical practitioner having an operator credential to perform a plurality of permitted software functions comprising operating the imaging device via the OR hub to capture an image or video of the patient during the surgical procedure, storing the image or video of the patient in a case file, and transmitting at least a portion of the case file to an external device via a preconfigured network connection, but preventing the medical practitioner from changing one or more imaging device access privileges of the OR hub, changing the preconfigured network connection, and changing the plurality of permitted software functions;
permitting, via the operations UI, a hospital network administrator having an administrator credential to change the operator credential of the medical practitioner, access audit logs comprising information related to usage of the permitted software functions including metadata generated at the OR hub based on user interactions with the operations UI, and change the preconfigured network connection, but preventing the hospital network administrator from changing the plurality of permitted software functions; and
permitting a hub software developer having a developer credential to configure the plurality of permitted software functions, wherein the operations UI is configured to prevent any hospital personnel having the operator credential or the administrator credential from altering the metadata generated at the OR hub based on user interactions with the operations UI.

29. A method for improving cybersecurity of an operating room, comprising:
at an operating room (OR) hub storing patient data and coupled to one or more medical devices in the operating room and providing an operations user interface (UI), the one or more medical devices comprising an imaging device:
displaying, via the operations UI, a login prompt to a user to prevent a user from interacting with the imaging device until the user is authenticated during a surgical procedure on a patient;
in response to authenticating a medical practitioner as having an operator credential:
displaying, via the operations UI, a plurality of graphical elements that correspond to a plurality of permitted software functions, wherein a selection of a graphical element permits the medical practitioner to operate the imaging device via the OR hub to capture an image or video of the patient during the surgical procedure, store the image or video of the patient in a case file, or transmit at least a portion of the case file to an external device via a preconfigured network connection according to the selected graphical element, and wherein the medical practitioner is prevented from changing one or more imaging device access privileges of the OR hub, changing the preconfigured network connection, and changing the plurality of permitted software functions;
in response to authenticating a hospital network administrator as having an administrator credential:
displaying, via the operations UI, a panel that permits the hospital network administrator to change the operator credential of the medical practitioner, access audit logs comprising information related to usage of the permitted software functions including metadata generated at the OR hub based on user interactions with the operations UI, and change the preconfigured network connection, wherein the hospital network administrator is prevented from changing the plurality of permitted software functions; and
in response to authenticating a hub software developer as having a developer credential:
permitting the hub software developer to configure the plurality of permitted software functions, wherein the operations UI is configured to prevent any hospital personnel having the operator credential or the administrator credential from altering the metadata generated at the OR hub based on user interaction with the operations UI.

30. A non-transitory computer-readable storage medium comprising one or more programs for improving cybersecurity of an operating room using an operating room (OR) hub storing patient data and connected to one or more medical devices in the operating room, the one or more medical devices comprising an imaging device, wherein the one or more programs, when executed by one or more processors, cause the one or more processors to perform operations comprising:
preventing a user from interacting with the imaging device until the user is authenticated though an operations user interface (UI) during a surgical procedure on a patient;
permitting, via the operations UI, a medical practitioner having an operator credential to perform a plurality of permitted software functions comprising operating the imaging device via the OR hub to capture an image or video of the patient during the surgical procedure, storing the image or video of the patient in a case file, and transmitting at least a portion of the case file to an external device via a preconfigured network connection, but preventing the medical practitioner from changing one or more imaging device access privileges of the OR hub, changing the preconfigured network connection, and changing the plurality of permitted software functions;
permitting, via the operations UI, a hospital network administrator having an administrator credential to change the operator credential of the medical practitioner, access audit logs comprising information related to usage of the permitted software functions including metadata generated at the OR hub based on user interactions with the operations UI, and change the preconfigured network connection, but preventing the hospital network administrator from changing the plurality of permitted software functions; and permitting a hub software developer having a developer credential to configure the plurality of permitted software functions, wherein the operations UI is configured to prevent any hospital personnel having the operator credential or the administrator credential from altering the metadata generated at the OR hub based on user interaction with the operations UI.

* * * * *